(12) United States Patent
Mac Quarrie et al.

(10) Patent No.: US 12,201,432 B2
(45) Date of Patent: Jan. 21, 2025

(54) TRI-AXIAL SEISMOCARDIOGRAPHY DEVICES AND METHODS

(71) Applicant: LLA Technologies Inc., Kelowna (CA)

(72) Inventors: David S Mac Quarrie, Langley (CA); John Patrick Neary, Regina (CA); Robert David Sauchyn, Regina (CA)

(73) Assignee: LLA TECHNOLOGIES INC., Kelowna (CA)

( * ) Notice: Subject to any disclaimer, the term of this patent is extended or adjusted under 35 U.S.C. 154(b) by 0 days.

(21) Appl. No.: 17/081,287

(22) Filed: Oct. 27, 2020

(65) Prior Publication Data
US 2022/0125330 A1    Apr. 28, 2022

(51) Int. Cl.
*A61B 5/00* (2006.01)
*A61B 5/02* (2006.01)
(Continued)

(52) U.S. Cl.
CPC ............ *A61B 5/341* (2021.01); *A61B 5/0022* (2013.01); *A61B 5/02028* (2013.01);
(Continued)

(58) Field of Classification Search
CPC ........................ A61B 5/349; A61B 2562/0219
See application file for complete search history.

(56) References Cited

U.S. PATENT DOCUMENTS

| | | | |
|---|---|---|---|
| 2013/0109989 A1* | 5/2013 | Busse ................. | A61B 5/7282 600/527 |
| 2013/0172771 A1* | 7/2013 | Muhlsteff ........... | B60R 25/1004 600/534 |

(Continued)

FOREIGN PATENT DOCUMENTS

| | | |
|---|---|---|
| FI | 000126008 B | 5/2016 |
| WO | 2020205987 A1 | 10/2020 |

OTHER PUBLICATIONS

Exploring Heartbeat Sub-patterns for Person Identification, Carreiras et al., Conference: RecPad 2013—Portuguese Conference on Pattern Recognition (Year: 2013).*

(Continued)

*Primary Examiner* — Sana Sahand
(74) *Attorney, Agent, or Firm* — YOUNG LAW FIRM, P.C.

(57) ABSTRACT

A computer-implemented method may comprise providing a wireless tri-axial seismocardiography (SCG) device configured to measure and time-stamp movements of a user's chest caused by the user's heart beats; positioning the SCG device on the user's chest in a predetermined orientation and initiating a test; using the positioned SCG device, detecting, sampling, digitizing and time-stamping movement vectors of the user's chest over a predetermined period of time in each of x, y and z directions; storing the time-stamped digitized movement vectors in a memory of the SCG device and sending the time-stamped digitized movement vectors to at least one of the app on the mobile device and the remote server over a computer network; receiving, by the app on the mobile device, a plurality of fiduciary markers from the remote server, the plurality of fiduciary markers being detected from or derived using the time-stamped digitized movement vectors in each of x, y and z directions; and generating a report on the mobile device using at least some of the plurality of fiduciary markers, the report including an indication of the health of the user's heart.

18 Claims, 14 Drawing Sheets

(51) Int. Cl.
    A61B 5/11      (2006.01)
    A61B 5/259     (2021.01)
    A61B 5/341     (2021.01)
    A61B 5/349     (2021.01)
    G06V 40/10     (2022.01)
(52) U.S. Cl.
    CPC ............ *A61B 5/1102* (2013.01); *A61B 5/259* (2021.01); *A61B 5/349* (2021.01); *A61B 5/7246* (2013.01); *G06V 40/15* (2022.01); *A61B 5/6831* (2013.01); *A61B 2560/045* (2013.01); *A61B 2562/0219* (2013.01)

(56) References Cited

U.S. PATENT DOCUMENTS

| | | | |
|---|---|---|---|
| 2014/0066798 | A1 | 3/2014 | Albert et al. |
| 2015/0038856 | A1 | 2/2015 | Houlton et al. |
| 2015/0133806 | A1 | 5/2015 | Airaksinen |
| 2016/0217565 | A1* | 7/2016 | Mozer ................. A61B 5/117 |
| 2016/0220152 | A1 | 8/2016 | Meriheina |
| 2017/0238847 | A1 | 8/2017 | Inan et al. |
| 2017/0347899 | A1 | 12/2017 | Bhushan et al. |
| 2018/0035919 | A1 | 2/2018 | Koivisto |
| 2018/0214030 | A1 | 8/2018 | Migeotte et al. |
| 2019/0314192 | A1* | 10/2019 | Raj ..................... A61B 5/0002 |
| 2019/0365263 | A1 | 12/2019 | Raj et al. |
| 2020/0029834 | A1* | 1/2020 | Tang ................. A61B 5/14552 |
| 2021/0315463 | A1 | 10/2021 | D'Mello |

OTHER PUBLICATIONS

Teckchandani T.A., MacQuarrie, D.S., Singh, J., Neary, J.P. (2020). Effects of Normobaric Hypoxia on Cardiac Mechanical Function Using Seismocardiography. Proc. SPIE 11237, Biophotonics in Exercise Science, Sports Medicine, Health Monitoring Technologies, and Wearables, 112370E (Feb. 21, 2020); doi: 10.1117/12.2546378, 8 pages.

Vogt, E.S.M., MacQuarrie, D.S., Neary, J.P. (2012). Using ballistocardiography to measure cardiac performance: a brief review of its history and future significance. Clin Physiol Funct Imag, 32:415-420.

Neary, J.P., MacQuarrie, D.S., Jamnik, V., Gledhill, N., Gledhill, S., Busse, E.F. (2011). Assessment of mechanical cardiac function in elite athletes. The Open J Sports Med; 5:38-44.

Singh, J., Neary, J.P., MacQuarrie, D.S. Cardiac function following sport-related concussion: Case study using seismocardiography, Canadian Society for Exercise Physiology, Oct. 25-28, 2017, Winnipeg, BC. 1 page.

Silbernagel, J., Ludlow, M., Balbar, M., Dinh, A., MacQuarrie, D.S., Ko, SK, Neary, J.P. Using seismocardiography to assess systolic timing intervals pre and post-exercise training in heart failure: A pilot study. Can Assoc Cardiac Rehab, Oct. 24-26, 2013. Montreal, PQ. 1 page.

Neary, J.P., MacQuarrie, D.S., Gebhardt, V. Relationship Between Seismocardiography and Echocardiography for Measuring Cardiac Cycle Timing Events. Physiol Society, Oxford, UK, Jul. 11-14, 2011. 2 pages.

Macquarrie, D.S., Gebhardt, V., Neary, J.P. Comparison of Seismocardiography to Echocardiography for Measuring Cardiac Cycle Events. Eur College Sports Sci, Liverpool, UK, Jul. 6-9, 2011. 2 pages.

Neary, J.P., MacQuarrie, D.S., Busse, E.F. Cardiac contractility and performance can be reliably measured day-to-day using digital ballistocardiography. Med Sci Sports Exerc 42 (Supplement):S379, 2010. 2 pages.

Macquarrie, D.S., Neary, J.P. Myocardial dysfunction and cardiac performance in marathon runners monitored using ballistocardiography. ACSM Integrative Physiol of Exerc, Miami FL, Sep. 22-25, 2010. 2 pages.

Vogt, E.S.M., Neary, J.P., MacQuarrie, D.S., Jamnik, V., Gledhill, N. Detecting effects of physical training on cardiac performance using non-invasive ballistocardiography. CSEP Annual Conference and Meetings, Toronto ON, Nov. 3-5, 2010. 1 page.

Len, T.K., Neary, J.P., MacQuarrie, D.S., Vogt, E.S., Goodman, D., Busse, E.F. Detecting changes in autonomic function following sport concussion in adolescent male athletes using digital ballistocardiography. EPOWC Conference, Regina SK, Aug. 12-14, 2010. 1 page.

Neary, J.P., MacQuarrie, D.S., Jamnik, V., Gledhill, N., Gledhill, S., Busse, E.F. Hypertrophic cardiomyopathy in an elite hockey player: Using digital ballistocardiography to confirm echocardiography and MRI. Appl Physiol Nutr Metab 34 (Supplement):S67, 2009. 1 page.

Neary, J.P., MacQuarrie, D.S., Busse, E.F. Cardiac cycle timing events are reliably measured day-to-day using digital ballistocardiography. Physiol Soceity Proc, Dublin, PC202, 2009. 1 page.

Neary, J.P., Len, T.K., Busse, E.F., MacQuarrie, D.S., Goodman, D.G. Using digital ballistocardiography (dBG) to detect autonomic nervous system changes in the concussed athlete. Brit J Sports Med 43 (Supplement): i93, 2009. 1 page.

Vogt, ESM, Neary JP, MacQuarrie DS, Len TK, Busse EFG. Detecting effects of obesity and diabetes mellitus on cardiac performance using digital ballistocardiography. Appl Physiol NutrMetab 34 (Supplement):S99, 2009 1 page.

Len, T.K., Neary, J.P., MacQuarrie, D.S., Vogt, E.S.M., Goodman, D., Busse, E.F.G. Detecting changes in autonomic function following sport concussion in adolescent male athletes using digital ballistocardiography. Appl Physiol NutrMetab 34 (Supplement):S55, 2009. 1 page.

Neary, J.P., Len, T.K., MacQuarrie, D.S., Jamnik, V., Gledhill, N., Busse, E.F. Cardiac characteristics of elite prospect hockey players: A digital ballistocardiography study. Appl Physiol Nutr Metab 33 (Supplement S70), 2008. 1 page.

Neary, J.P., MacQuarrie, D.S., Busse, E.F. Impaired cardiac timing events post marathon as detected using digital ballistocardiography. Am Physiol Society Proc, p33, Hilton Head, S.C., 2008. 1 page.

Neary, J.P., Len, T.K., MacQuarrie, D.S., Busse, E.F. Cardiac function during maximal incremental exercise in varsity athletes using digital ballistocardiography. Physiol Society Proc, Cambridge, 59P, UK., 2008. 2 pages.

Neary, J.P., Busse, E.F., MacQuarrie, D.S., Goodman, D. Using digital ballistocardiography to detect autonomic nervous system changes in the concussed athlete. Eur Congress Sport Sci, p. 517, Estoril, Portugal, 2008. 3 pages.

Neary, J.P., Len, T.K., MacQuarrie, D.S., Busse, E.F. Mechanical changes in cardiac function during maximal incremental exercise in varsity athletes using digital ballistocardiography. Regina Qu'Appelle Health Region Showcase Conference, Regina, 2008. 2 pages.

International Search Report and Written Opinion of the International Searching Authority dated Apr. 20, 2022 in PCT/IB2021/000743.

* cited by examiner

SCG Report Card

LLA TECHNOLOGIES INC.

Heart Rate 63 bpm

Heart Rate Variability 7.5 RMSSD [bpm]
5.5 SDNN [bpm]

| | | Range | | SD |
|---|---|---|---|---|
| | | 30 – 80 bpm | | 5.5 bpm |
| Systolic Time | 276 ms | 199 – 502 ms | | 28.3 ms |
| Diastolic Time | 528 ms | 295 – 1507 ms | | 134.6 ms |
| Isovolumetric Contraction Time | 73 ms | 35 – 129 ms | | 21.9 ms |
| Isovolumetric Relaxation Time | 94 ms | 36 – 167 ms | | 19.4 ms |
| Rapid Ejection Time (Systole) | 73 ms | 48 – 134 ms | | 11.9 ms |
| MVO to Early Diastolic Wave Time (Diastole) | 47 ms | 22 – 91 ms | | 15.8 ms |

Signal Quality 97%

TRI-AXIAL SEISMOCARDIOGRAPHY DEVICES AND METHODS

BACKGROUND

Cardiac timing information has been used clinically since the 1900s and is a reliable indicator of cardiac performance and health. Myocardial relaxation and contraction are coordinated by the intracellular recycling of calcium ions. The timing of these cardiac events is related to the health of the myocardial cells. Thus, the accurate measurement of specific cardiac events of the cardiac cycle is clinically significant.

The electrocardiogram (ECG) is most often used in clinical settings for initial cardiac diagnosis. The ECG provides a representation of the electrical behavior of the heart and has been used successful to screen large healthy populations, such as for sport teams. However, ECG is not always reliable to assess cardiac problems. ECG in the case of athletes may not detect a variety of conditions such as coronary artery disease, hypertrophic cardiomyopathy and mitral valve prolapse. Echocardiography, using standard two-dimensional M-mode and Doppler ECHO, is commonly used to evaluate cardiac performance. ECHO is considered the "gold standard", but for routine assessment, initial screening, or group testing of sport teams, it is costly and requires technical specialists to conduct the testing and image analysis.

Seismocardiography (hereafter, SCG) was originally described in 1877. One of the first use cases of SCG was in 1939, using a device that measured the head to foot, or longitudinal motions (x-axis) of the body created by cardiac contraction, and the method was then termed ballistocardiography (BCG). The seismocardiogram differs in that it measures the transverse or sternal vibrations (z-axis) that go from anterior to posterior of the chest. SCG, therefore, is said to measure the reaction force caused by ejection of the blood. SCG reacts to the transverse deflections of the chest wall and is likely a superior modality to accurately reflect the opening and closing of the heart valves.

The ECG is useful in generating a representation of electrical activity of the heart when there is disease or when disease is suspected. This makes use of this technology inherently reactive in nature. What are needed, however, are devices, methods and technologies that enable the recording of cardiac data on a contemporaneous, immediate basis, as well as on a long term, or daily basis. What are also needed are devices, methods and technologies that enable medically-unsophisticated users to easily, quickly and inexpensively acquire medically-accurate and medically-relevant data responsive to particular physiological or emotional events, such as stress or trauma. Also needed are preemptive devices, methods and systems to monitor heart activity.

For instance, a user might want to start an exercise program or reduce stress, which activity would create changes in the performance of the heart, which would be cumulative over time. Another example relates to changes in blood pressure. Conventional ECG will not show such changes until the person on whom the ECG is used becomes hypertensive. The ECG cannot show timing changes in the heart immediately along with the force of each contraction and thus cannot, in itself, be readily used to guide users in making positive lifestyle changes. Methods, devices and systems for generating and storing detailed snapshots and recordings of cumulative changes over time of heart health would address such needs.

With an increase in COVID-19 cases (more than 42.2 million as of this writing in October 2020), there is a great demand for research to help alleviate some of the financial and personnel burden on the health care systems. The most recent research related to the COVID-19 virus has confirmed its lethal effect on the heart, cardiovascular and respiratory systems, with some reports stating more than 50% of the deaths are cardiac-related. Thus, it is imperative that the research community provide more details as to the underlying physiological changes and the mechanisms causing cardiac dysfunction as a result of the COVID-19 virus. This will aid practitioners to better diagnose, triage, and treat patients in as little time as possible. Case reports of impaired systolic function related to the coronavirus have been reported. Furthermore, other case reports have suggested that those afflicted with COVID-19 may be at increased risk of developing myocarditis and heart failure. Increases in high-sensitivity cardiac troponin-I can be associated with COVID-19, and cardiac troponin-I changes can also be associated with SARS-CoV-2, suggesting a case for acute cardiac injury.

It has been suggested that echocardiography can be used to assess and diagnose cardiac complications related to COVID-19. Thus, an urgent need exists for devices, systems and methods to monitor cardiac health in large populations, populations that are not and cannot be well served by existing ECG devices.

BRIEF DESCRIPTION OF THE DRAWINGS

FIG. 8 shows an exemplary SCG Report Card that may be generated from an SCG device, according to one embodiment.

DETAILED DESCRIPTION

Figure 1:
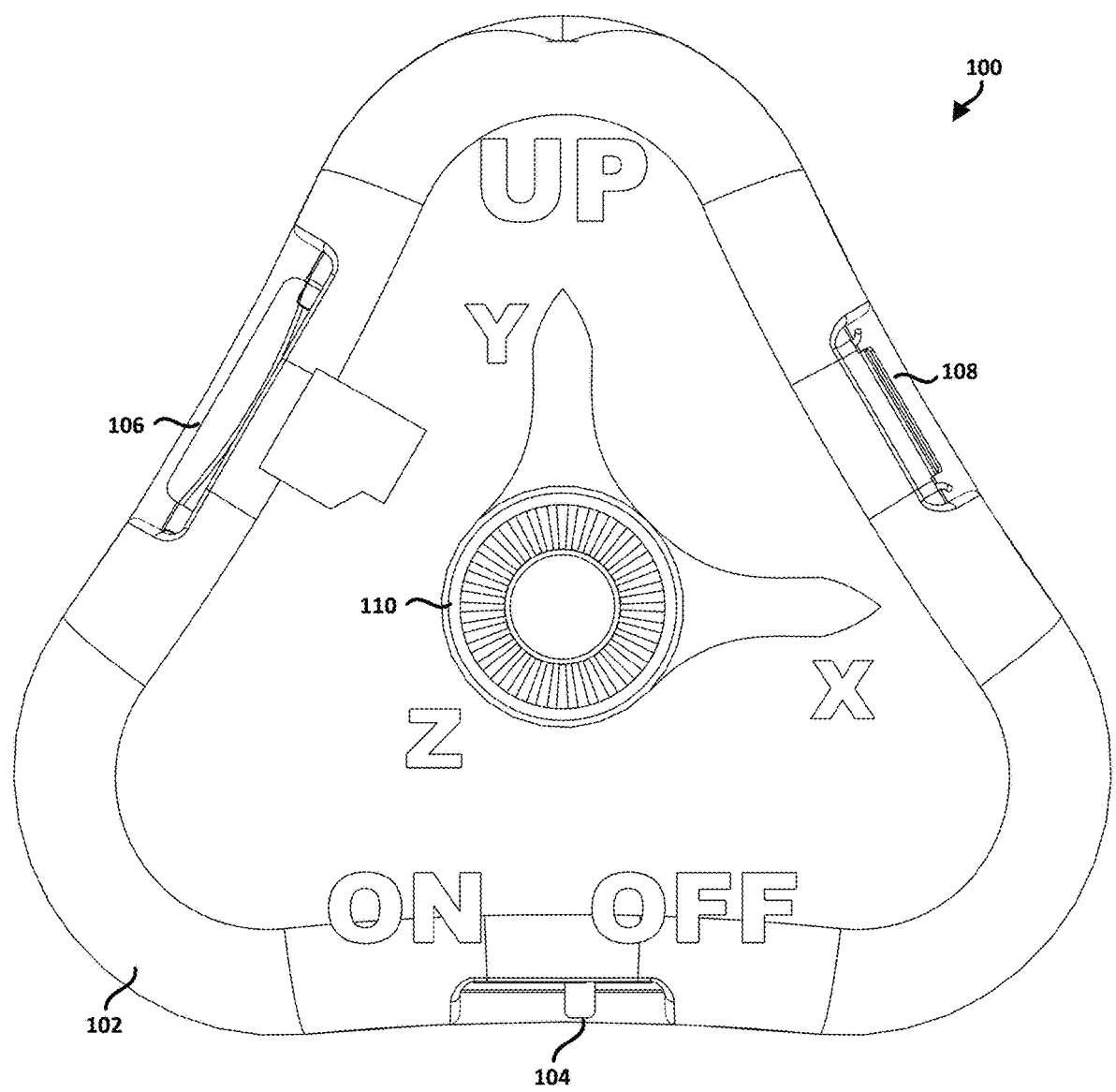
FIG. 1 is a first view of an SCG device according to one embodiment.

A heart at rest produces a reliable predictable seismic pattern that can be compared with the seismic pattern generated by the heart from rest through exercise. Embodiments provide accurate and immediate feedback to both individuals and large populations on the health and daily functioning of their heart (i.e., cardiac performance) through seismic three-axis data that is easily acquired and stored. According to embodiments, in-depth measures may be generated of all aspects of the status and quality of the heart's contractions and relaxations (the mechanical function of the heart), and of the manner in which the heart and the brain interact during times of stress (the heart rate variability, HRV). Values measured and stored by devices according to embodiments compare favorably with the "Gold Standard" benchmark method of measuring cardiac performance, Echocardiography (ECG). A light (on the order of a few tens of grams), small, portable and handheld device according to an embodiment requires only a short period of time (e.g., about a minute) to acquire and store data, whereas an echocardiogram study takes 40 to 45 minutes and requires very complex technology and the specialized infrastructure and trained personnel of a cardiac care center. The cardiac data acquired and stored by a device according to an embodiment enables tracking changes in heart health by the user, through his or her mobile device, for example. The convenience and rapidity with which devices according to embodiments acquire and store heart data enables them to track cardiac health over time, and enables users to make informed, contemporaneous and data-driven effective lifestyle choices and decisions concerning their health and/or identify working conditions that may be causing long-term negative changes in the heart.

One embodiment is a small device that includes a number of small sensor and a communication package and that may be pressed against the user's body for a short period of time, to measure a number of cardiac points of interest—also called fiduciary markers herein. One embodiment of the device comprises ultra-sensitive micro accelerometers to measure seismic waveforms caused by the movement of the heart in the user's chest.

As noted above, when the heart is under load, it produces a simple repeatable seismic pattern. A healthy heart under load increases the force of contraction and, therefore, the corresponding amplitude and slope of the resulting seismic waveforms increases as well, together with a reductions in the cardiac timing intervals. The present device is extremely sensitive to slight changes in the magnitude and direction of velocity and force vectors on the user's chest wall caused by the contractions of the heart, and is also highly sensitive to the time intervals needed to reach the maximum accelerations. When these waveforms produce lower amplitude signals, or signals of shallower slope under load or effort, such measures are highly specific for detecting reduced cardiac performance. These changes are progressive throughout the exercise for those with disease and throughout their lifetime. The changes in speed of acceleration cause changes in critical timing intervals that can indicate systolic (emptying) and (diastolic) changes in the pumping efficiency of the heart.

Figure 2:
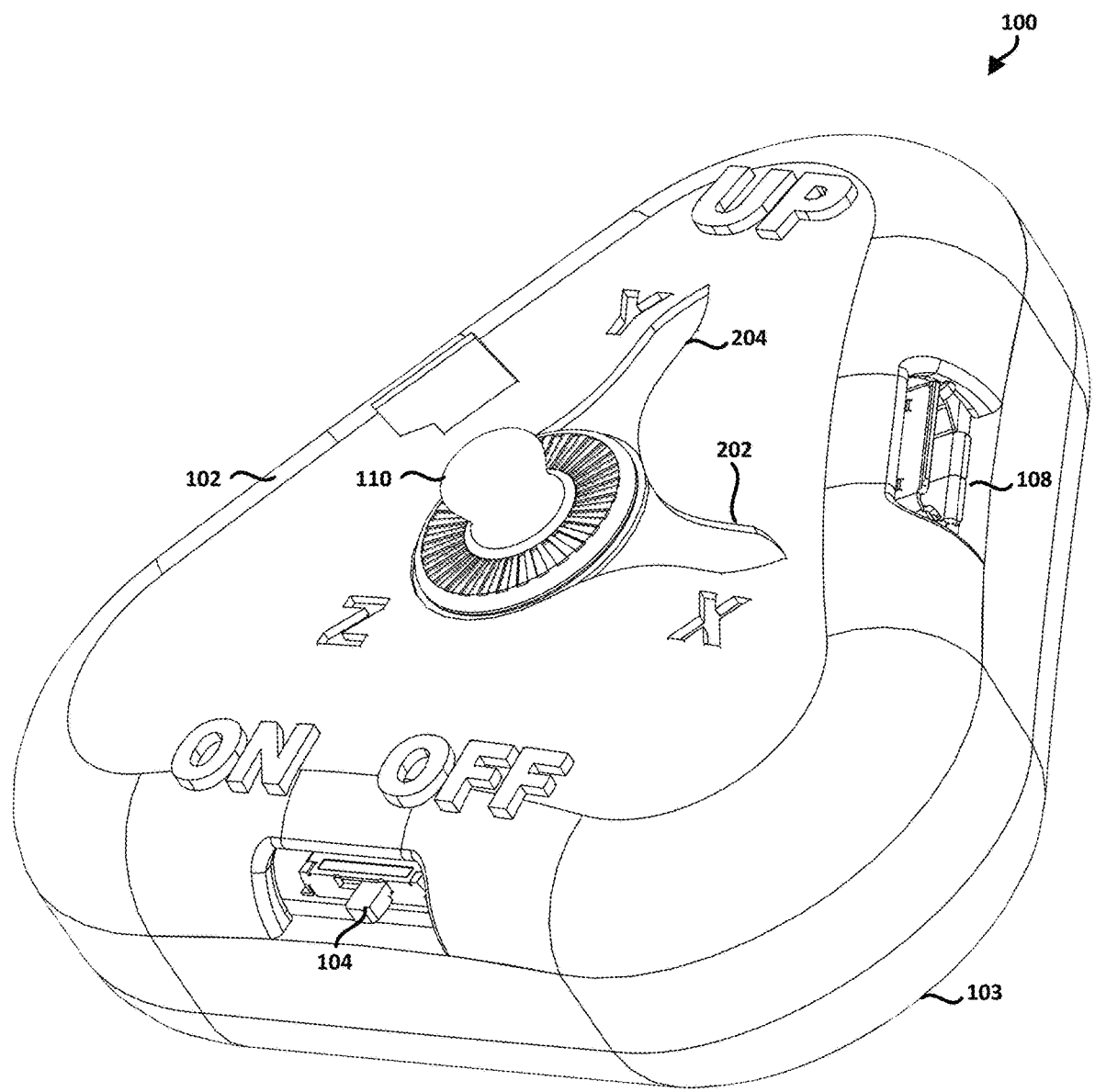
FIG. 2 is a second view of an SCG device according to one embodiment.
Figure 3:
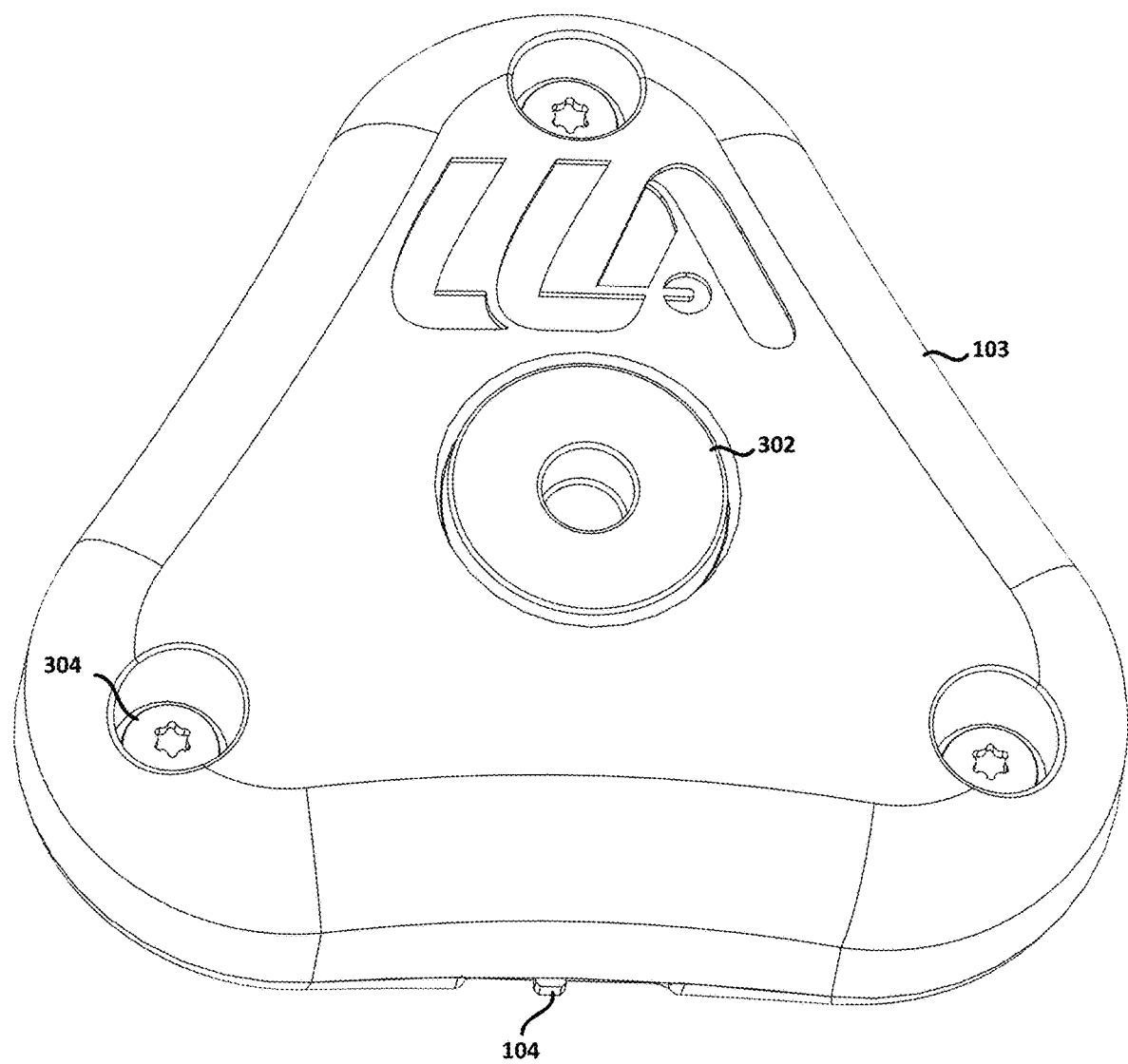
FIG. 3 is a third view of an SCG device according to one embodiment.

FIGS. 1, 2 and 3 shows various views of an SCG device 100 according to one embodiment. The SCG device 100 includes a sensitive triaxial accelerometer to measure the acceleration of parts of the human body produced by the heart. The SCG device 100 may (but need not) be roughly triangular in shape, with one of the vertices thereof pointing in the y-axis direction; that is, along the head-to-feet direction. Arrows indicating the x, y and z axes may be impressed on the housing, which may comprise a first half 102 facing away from the user and a second half 103 facing and configured to come into intimate contact with the user's skin. An arrow indicating the x-axis may be provided, which indicates the spatial axis aligned with left and right arms, normal to the y-axis. Lastly, the z-axis is away from and back towards the user's chest, and is aligned generally with the central axis of the chest snap strap 602 (shown in FIG. 6), perpendicular to both the x- and y-axes. An on/off switch may be provided at 104, as may be a charging port 108. A port for a removable non-volatile memory may be provided at 106.

Figure 4:
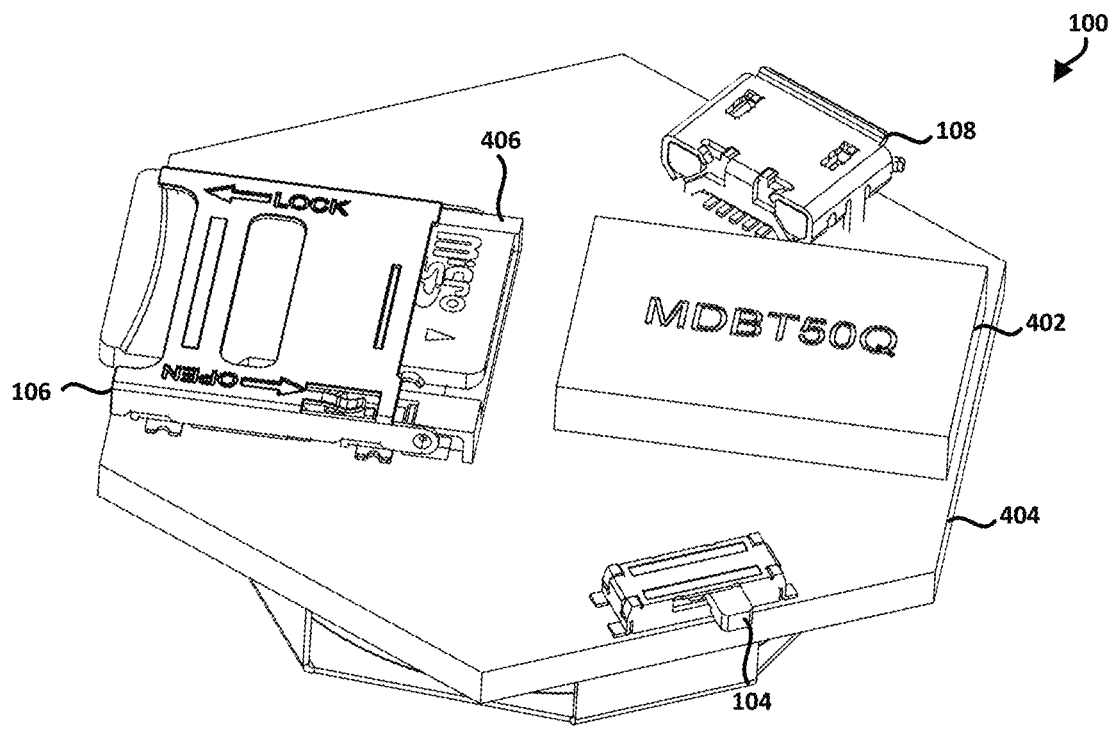
FIG. 4 shows elements of an SCG device according to one embodiment.
Figure 5:
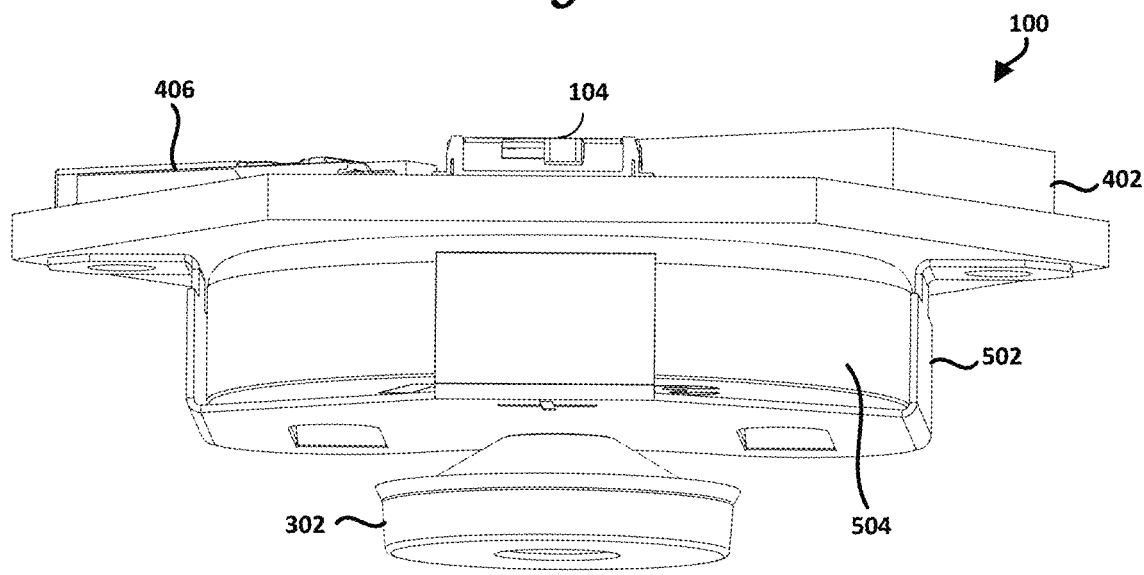
FIG. 5 shows other elements of an SCG device according to one embodiment.

FIGS. 4 and 5 show elements of an SCG device according to one embodiment. As shown therein, the SCG device 100 is shown without the first and second halves 102, 103 of the housing, showing the contained elements. A printed circuit board, shown in simplified form at 404, supports a processor at 402, the removable memory port 106 and its contained memory card 406, the charging port 108 and the on/off switch 104. The processor 402 may include a number of communication interfaces configured to enable sensors to connect thereto and to facilitate data transfer to the outside world. As shown in FIG. 5, attached to the underside of the PCB 404 is a battery bracket 502 configured to secure a coin-sized battery 504 there against. A skin contact surface 302 is also provided, and configured to conduct seismic forces from the user's chest to the tri-axial accelerometers. A tri-axial accelerometer (not shown in FIGS. 4 and 5) is also coupled to the PCB 404, as detailed below.

Using the SCG Device

Figure 6:
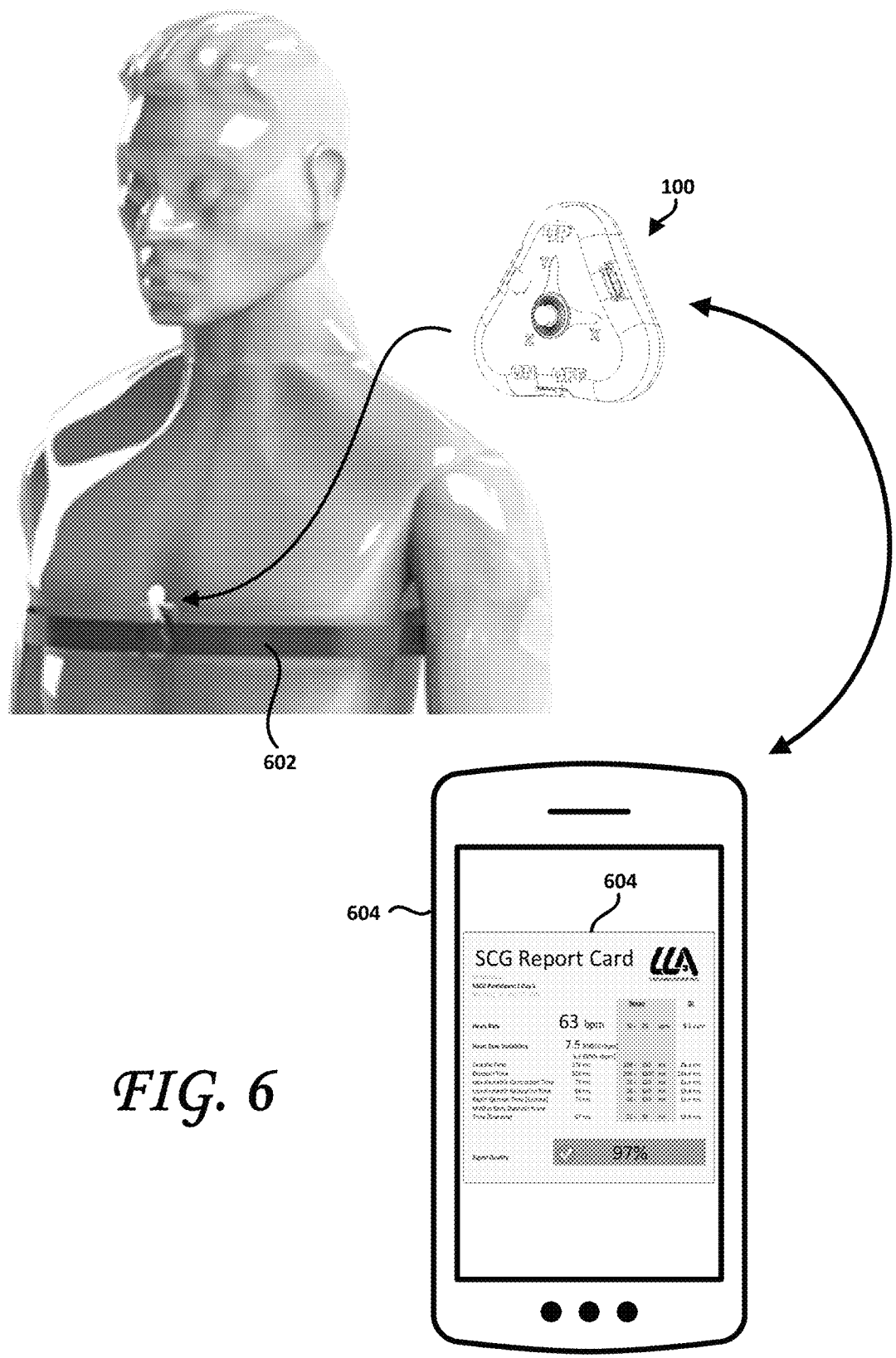
FIG. 6 shows an SCG device according to an embodiment, in use.

Wide adoption and regular use of the present SCG device is believed to be predicated upon usability and convenience. Toward that end, one embodiment is the size of a large coin is configured to non-invasively sit on the user's sternum during the test. To promote usability, the test may be initiated by an app on the user's mobile device, whereupon the sensors of the SCG device collect the cardiac data and wirelessly transmit the data to the mobile device. The data may then be encrypted and, in one embodiment, sent to a secure remote server for automatic analysis, as shown in FIGS. 9-15. Thereafter, a report as shown in FIGS. 6 and 8 may be generated and stored. Once a baseline test has been recorded, improvements or deterioration in cardiac performance may be tracked and reported each time the user undergoes a subsequent test.

Upon receiving a new SCG device according to an embodiment, the user will download the app for his or her mobile device. Upon first opening the app, the user will be asked to enter a User ID. The SCG device may then be turned on, whereupon the SCG device will wirelessly connect to the mobile device app, via a short distance communication protocol such as Bluetooth or some other NFC protocol. The date and time may then be set, along with the local time zone. In one embodiment, the collected heart data is stored on the SCG device's microSD card, as shown at 406 in FIGS. 4 and 5. Other storage devices may be used. Afterwards, the user's encrypted data may be uploaded to the "cloud" (e.g., the remote server(s) discussed herein) using the app at any time. This enables the user to collect data even when there is no network access point, Wi-fi or 5G signal available. Therefore, the present SCG device 100 may be used in conjunction with the mobile device app or by itself, storing the acquired data for later transmission, analysis and reporting. The app can connect to the SCG device 100 any time, as long as the SCG device 100 is turned on.

With reference to FIG. 6, when ready to start recording, the user may snap the SCG device to a supplied chest strap 602 and may secure the SCG device 100 to his or her chest, making sure that the skin contact element 302 (FIGS. 3, 5) sites firmly on the skin. Also, the SCG device 100 should be oriented such that the bottom edge is over the top of the xiphoid process (the soft cartilage piece that 'hangs-off' the sternum) and such that the "UP" letters (FIGS. 1 and 2) face away from user's chest and such that the y-axis arrow in the housing points toward the user's head. This will ensure that each of the x-, y- and z-axis accelerometers are oriented properly and record the correct spatial data.

To initiate the recording process, the user may start the mobile app on his or her mobile device 604. The SCG device 100 may then be turned on, using the switch 104 at the bottom of the device. Within a few seconds, an LED light should turn on and remain solid, indicating that the SCG device 100 is connected to the mobile device 604 and has begun recording seismic data. A countdown timer in the App will then start a 5 minute (for example) countdown. A flashing on the LED indicates that the 5:00 minute test recording session has ended. Once the cardiac data has been successfully collected, the app will so indicate.

Device Hardware

Figure 7:
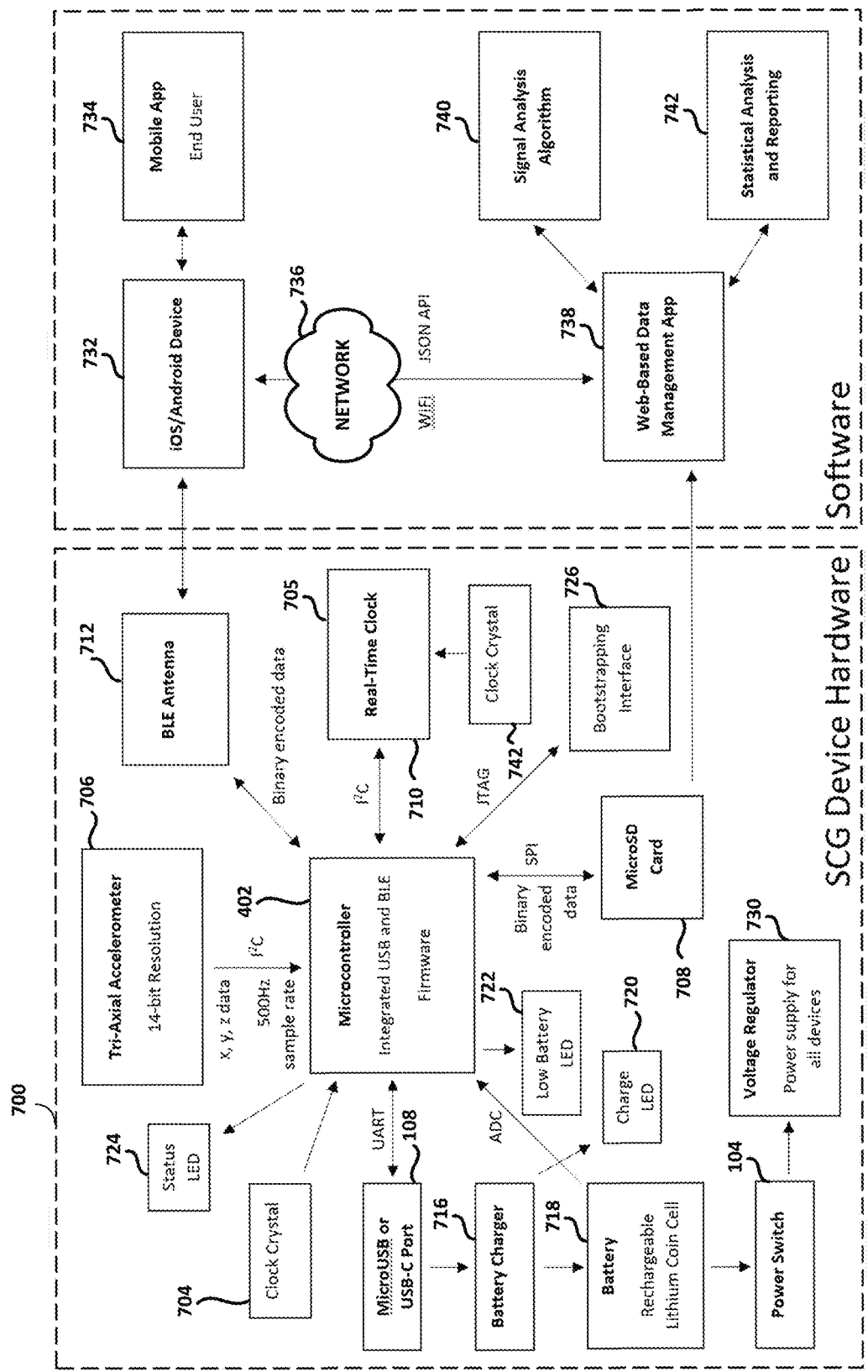
FIG. 7 is a block diagram of aspects of the hardware and software of an SCG device according to one embodiment.

FIG. 7 is a block diagram of the physical device hardware and the software of the present SCG device 100 that is configured to interact with the hardware and enable the functionalities described and shown herein, according to an exemplary implementation. An SCG device 700, according to one embodiment, may include the elements shown in FIG. 7 or functional equivalents thereof, in a small, light (e.g., about 30 grams) plastic housing (best shown in FIGS. 1, 2 and 3) the size of a large coin. A microcontroller 402 is provided, powered by a battery 718. The battery 718 may be a rechargeable battery, in which case, a charging port may be provided and accommodated in the housing. In one implementation, the battery (reference 504 in FIG. 5) is a LIR2450 3.6 volt lithium ion rechargeable coin-sized and shaped battery. The charging port may be a MicroUSB or USB-C port as shown at 108 coupled to a battery charger 716. Other communication and/or power transfer protocols may be used, as those of skill in this art may appreciate. A power switch 104 may be provided, to enable the SCG device 700 to be turned on and off. The switch 728 may be manual or may be programmatically-actuated. A voltage regulator 730 ensures that correct, clean voltages are supplied to all constituent elements of the device 700. Status and charge indicators 714, 720 may also be provided, to inform the user of the status of the device and its state of charge. A low battery indicator 722 may also be provided, which may actuate when insufficient charge remains to reliably acquire cardiac SCG data. A separate memory 406 may be provided, to store the acquired SCG data and to provide that SCG data on demand. In one embodiment, the memory 406 is non-volatile, such as Flash memory. In one implementation, the memory 406 is a MicroSD memory card. A bootstrapping interface 726 is provided, to enable the software implementing the functionality described herein to be loaded onto the microcontroller 402, via an integrated USB interface over a Universal Asynchronous Receive Transmit (UART) connection, for example. For example, the bootstrapping interface 726 may comprise eight small conductive pads exposed on the edge of the printed circuit board (shown in simplified form at reference 404 in FIG. 4) on which the microcontroller 402 is mounted, to enable the bootstrapping device to connect thereto, via a JTAG protocol, for example, to flash the operating program stored in the bootstrapping interface 726 onto the microcontroller 402. An RF antenna 712 may be provided, enabling the device 100 to communicate with a user's mobile device. In one implementation, the antenna 712 may be configured as a Bluetooth Low Energy (BLE) antenna, enabling the establishment of a short-range, high frequency wireless personal area network. The microcontroller 402 may include firmware to support both the USB and BLE (and/or others) communication protocols. Indeed, other short-range communication protocols may also be implemented. A first clock crystal 704 may be provided, to provide a time base for the microcontroller 402. In one implementation, the clock crystal 704 is a high frequency (e.g., 32 MHz) crystal to drive the timing of the microcontroller 402. Another clock crystal 742 may be provided, to drive the real-time clock 705. The clock crystal 742 may provide oscillations at, in one implementation, 32.768 kHz to the real-time clock 705, which may be configured to reliably keep the date and time for a long period of time (e.g., a few years), regardless whether the device 100 is on or off. The real-time clock 705 may be used to time-stamp cardiac data with high precision and to accurate enable time-based measurements of various cardiac parameters. The real-time clock 705 may communicate with the microcontroller 402 over, for example, a two-wire interface such as the $I^2C$. communication interface. In one implementation, the microcontroller 402 is a MDBT50Q SoC microcontroller manufactured by Seed Technology Co., Ltd., which is a 32-bit ARM® Cortex™ M4F CPU with 1 MB Flash Memory/256 kB RAM, 48 General Purposed Input output (GPIO) pins, and supports a number of low power wireless communication protocols, in addition to SPI, UART, I2C, I2S, PWM, ADC, NFC, and USB interfaces. Other implementations may utilize other microcontrollers.

One embodiment comprises multi-axis accelerometers that measure the effects on the user's chest of the motions of the heart as it moves toward and away from the chest, left to right, and head to foot. Time-stamped spatial data, as well as the first and second derivatives thereof may be acquired and/or calculated, to provide time-stamped position, velocity and acceleration heart data. As shown in FIG. 7, the microcontroller 402 may be coupled to a three-axis accelerometer 706. As the heart changes in position and as the large vessels (e.g., the aortic arch) change positions, these spatial changes induce small current waveforms in the accelerometers, which induced current waveforms are then sampled, quantized and sent to the microcontroller for storage in on-board memory device (e.g., MicroSD card 708). Alternatively, the digitized waveforms may be transmitted immediately via an app on a user's mobile device for remote analysis and reporting. The tri-axial accelerometer 706 may be coupled to a skin contact element (reference 302 in FIG. 3), configured to be pressed firmly onto the skin over the patient's sternum, as described herein. Using such a non-invasive sensor, the SCG device 100 measures the mechanical functioning of the heart, or in other words, how the valves open and close, how the blood flows through the heart, and how the heart twists and untwists in three dimensions as it contracts and relaxes. In so doing, the device 100 can measure the timing events of the heart's operation, from the closure of the aortic valve to the opening of the mitral valve, and the force of cardiac contraction, or contractility, for example. Indeed, as the heart beats, it moves left and right, up and down, and backward and forward in the chest, and the present SCG device 100, 700 collects data that enables a three-dimensional and time-based graphical reconstruction of these events to generated, by measuring the effect upon the user's chest of the movements of the cardiac muscle over all three x, y and z vectors. This allows the creation of a profile of systolic (emptying) and diastolic (filling) performance and the time required for each event at any given heart rate. Moreover, as the data is precision time-stamped, the heart rate can be measured at several points in the cardiac cycle (aortic valve open, mitral valve closed and mitral valve open).

According to one embodiment, the accelerometer 706 may be a high-sensitivity tri-axial accelerometer able to acquire acceleration data along all three axes at a sufficiently high rate to enable a fine-grained representation of the movement of the heart over time. Embodiments may be configured to measure accelerations of less than 1 mg and to sample all three spatial axes oftener than every 10 ms over a range greater than +/−0.5 g. In one implementation, the IMU of the tri-axial accelerometer 706 may be configured to sample all three spatial axes at 500 Hz, or once every 2 ms, at 14-bit resolution with a range of +/−2 g, meaning a resolution of $4/2^{14}=\sim 0.25$ mg, where g is the acceleration of gravity at sea level on Earth or about 9.8 m/sec$^2$. Coarser or finer-grained measurements may be acquired, by suitably configuring the device. For example, one suitable accelerometer is the low-power MMA8451 module manufactured by NXP Semiconductor. Advantageously, the MMA8451 includes both on-board high and low pass filtering functionality, to enable the device to filter out incidental low or high-frequency transients, respectively, events that may not be relevant to the analysis of cardiac activity. The PCB 404 may also include Wi-Fi connectivity via a Wi-Fi controller (ESP8266 or similar in one implementation) that interfaces a smartphone application to stream the data collected to a host on a computer network such as the Internet.

From the data collected by the accelerometer 706, one embodiment measures ten valuable points of interest (also referred to as fiduciary markers herein) in the cardiac cycle. These include atrial systole (AS), mitral valve closure (MVC), aortic valve opening (AVO), isovolumic contraction (IC), rapid ejection period (REP), aortic valve closure (AVC), mitral valve opening (MVO), and early diastole (E wave or rapid filling). From these points of interest, the following calculations can be made: isovolumic contraction time (IVCT), isovolumic relaxation time (IVRT), systolic ejection period and diastolic period. These values are diagnostic for distinguishing systolic and diastolic differences and are key to guiding interventions and early detection of cardiac performance issues. Changes of these values over time are good indicators of changes in the efficiency of the heart. Moreover, these timing results may be directly and favorably compared to those obtained from echocardiography.

The above-listed Atrial systole (AS) event may be identified as the negative peak of the Z-axis SCG data occurring after the P wave, a positive peak on the X-axis and a leftward shift on the Y-axis. The atrial systole may be identified as a positive deflection immediately preceding the Q-wave.

Mitral valve close (MVC) may be identified as the first peak following R wave of the ECG onset for the SCG marking, where the Z-axis has a large negative deflection, X-axis is positive and Y-axis is slightly leftward. This is followed by a large recoil signal due to flow from the coronary sinus. ECHO MVC is the point on the ECHO where the close signal is detected at the end of the rapid filling wave.

Aortic valve opening (AVO) may be identified as a leftward shift of the Y-axis, a positive deflection of the Z-axis and a positive deflection of the X-axis. It is the first vector change from the close of the mitral valve (MVC).

Acceleration time is identified as the first change in direction and return to baseline on the Z-axis and the confirming vector shift of the X-axis are defined as the end of the rapid acceleration period (REP). The REP of the SCG correlates to the peak flow signal on Doppler. This time period is reported in ECHO as pressure half time or acceleration time. This signal is created by a slight repositioning movement of the ventricle at the end of contraction which is detected on the SCG.

Aortic valve close (AVC) is the slope change on Z-axis that occurs near the end of the T-wave of the ECG. The Z-axis moves away from the chest, the X-axis moves footward and the Y-axis moves slightly rightward. In ECHO Doppler mode, AVC is measured as a distinct flash at cessation of flow.

Mitral valve open (MVO) corresponds to the second negative slope on the Z-axis following the aortic close signal. The X-axis moves footward. The signal is negative in the Z-axis negative in the X-axis and leftward in the Y-axis.

Early Diastolic filling wave or rapid flow corresponds to the second rounded peak following the mitral valve open point.

Left ventricular ejection time (LVET) may be calculated from the aortic valve open signal to the aortic valve close signal (AVO to AVC).

Diastole is defined as the period of time when the heart refills with blood after systole. The period is measured as the time from mitral valve open to mitral valve close in the next cardiac cycle (MVO to MVC).

Isovolumic contraction time (IVCT) is the time when all heart valves are closed and the volume in the ventricle is fixed prior to contraction and opening of the aortic and pulmonic valves it is measured from mitral valve close to aortic valve open (MVC to AVO). Experimental studies have shown that rapid left ventricular (LV) shape change during IVCT is essential for optimal onset of LV ejection. In terms of physical movement of the heart, IVCT measures the time from mitral valve close (found in the left side of the heart) to aortic valve open (which allows blood to leave the heart). This measurement is one of the measurements that may indicate whether the heart is experiencing contraction (systolic) problems, which affect the blood ejection from the heart, which can be related to blood pressure issues.

Isovolumic relaxation time (IVRT) is the isovolumic period that follows systole. All valves are closed and the time is measured from aortic valve close to mitral valve open (IVRT). This time is an indicator of diastolic or filling performance. Conceptually, IVRT is a short time interval between the end of aortic ejection (when the blood leaves the heart) and the beginning of when the ventricles begin to fill again. If this time gets longer, it may be surmised that the heart is beginning to experience additional stresses placed on the body, which stresses affect how the heart relaxes between beats. For example, increases in IVRT may be correlated with to blood pressure changes and/or increases in morning heart rate.

Mitral valve open to early diastolic filling wave is the time from the mitral valve open to maximum inflow to the ventricle (MVO to ED), which timing is important for monitoring diastolic performance. The time between MVO and ED is the time to fill the ventricles. The ventricles pump the blood to the lungs (via the right ventricle) and to the rest of the body (via the left ventricle). If this time gets longer, such an increase may indicate that the ventricles have become less receptive to the volume of blood they are receiving. In the younger population, this may be reversible with lifestyle changes, including exercise. In the older population these changes can be managed with highly effective drugs. These timing parameters, according to embodiments, may be provided in milliseconds and may be documented in a report made available to the user.

Rapid ejection time is a measure that is associated with the systolic or contraction performance of the heart. Taken together with both the IVRT and IVCT, the rapid ejection time provides vital information on the overall performance of the heart, and force with which the heart contracts. These measures may be recognized programmatically from the tri-axial time-based data recorded by the present SCG device. Supervised learning techniques, for example, may be leveraged to enable the ready identification of the above-enumerated parameters. Other methods, such as statistical analysis, may also be used.

As a result of calculating the above-identified measures, one embodiment generates a report for the user. Although each of the measures above may be made available to the user, such may not be the best way of communicating with lay people that are not medically trained. One embodiment, therefore, calculates and generates a Heart Performance Index (HPI), which is a combination of the IVRT, IVCT, and the Rapid Ejection Time measures and which provides the user with a simple, but accurate overall indication on the health or fitness of their heart. Both contraction and relaxation of the heart are important for heart health. If, over time, this number trends one way or the other, lifestyle changes (including nutrition, mental health and exercise) may be implemented to assist the user in maintaining a healthy heart, reduce any decline in heart health or indicate the need for a more interventional approach.

FIG. 8 shows an example of such a report 800 that includes the aforementioned HPI. Such a report 800 may include basic information, such as the heart rate and the variability thereof. Other measures may include, as shown in FIG. 8, systolic time, diastolic time, IVCT, IVRT, rapid ejection time (systole), MVO to early diastolic wave, and the ejection time (diastole). An HPI 802 may then be calculated from these (and/or other) measures, to provide an at-a-glance indication of cardiac health. In one embodiment, the report 800 may be provided on a user's mobile device or provided to a desktop computer, for example, via an email client. Systolic time is equal to AVO to AVC. Diastolic time is equal to Mitral valve close to mitral valve open. Isovolumic contraction is equal to mitral valve close to aortic valve open. Isovolumic relaxation is equal to aortic valve close to mitral valve open. Rapid ejection time is the time from aortic valve open to maximum flow in the ascending aorta. Mitral valve open to early filling wave is a measure of ventricular filling performance. In this implementation, the timings noted above are provided in milliseconds (ms).

Returning to FIG. 7, the acquired three-dimensional cardiac data may be stored in the memory 708 and/or transmitted over a wireless communication channel to a user's mobile device 732 running a mobile app 734. The received data may then be wirelessly transmitted over a network 736 (including, for example, the Internet), to a remote server using a JavaScript Object Notation (JSON) Application Program interface (API) encoding scheme. JSON API exposes an implementation for data stores and data structures, such as entity types, bundles, and fields. The JSON-encoded data received by the remote server may then be analyzed to detect the aforementioned cardiac measures as suggested at 740 and run through a statistical analysis and reporting module 742 to generate, among other items, the report 800 shown in FIG. 8. Alternatively or in addition, the acquired raw cardiac data (i.e., the time-stamped digitized movement vectors) may be stored in the non-volatile memory 708 and provided to the remote server running the web-based data management application 738 directly, bypassing the user's mobile device. The raw or processed data may then be made available to the user's physician in a HIPAA-compliant manner and/or integrated with health-based apps such as the Apple Health app, to identify but one possible candidate. Such data may also be provided and formatted to be displayed by the user's smartwatch for an at-a-glance health cardiac checkup.

Figure 9:
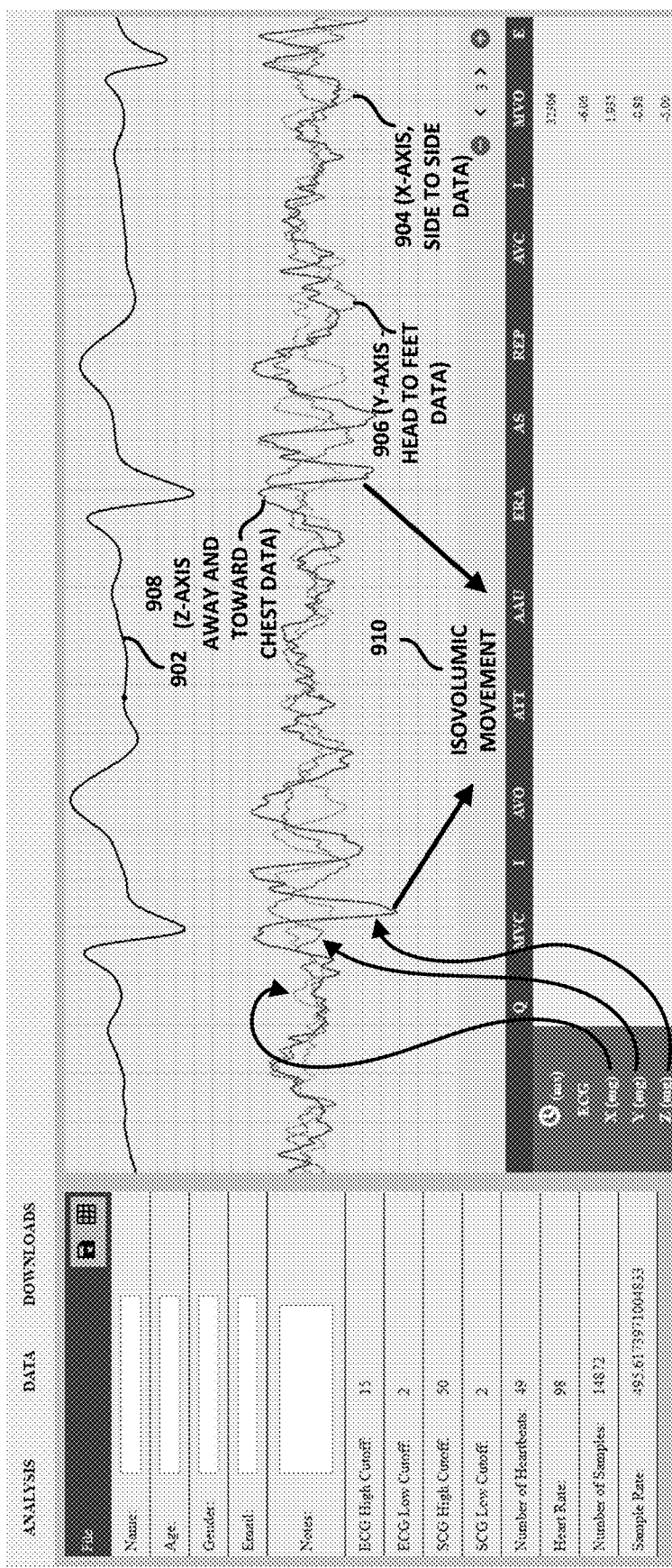
FIG. 9 shows a graph of the cardiac data acquired over time by an SCG device according to one embodiment, showing the identification of isovolumic movement.

FIG. 9 shows a graph of the acquired accelerometer cardiac data over time, such as may be used to identify and calculate and analyze cardiac parameters based upon the x, y and z data acquired by the SCG device 100. Herein, the axes follow the right-hand rule, with the x-axis corresponding to accelerometer data 904 logging movement from side to side, with movement toward the left arm being positive and toward the right arm being negative. The y-axis corresponds to accelerometer data 906 logging movement from aligned with the axis from the head to the feet, with heart movement toward the head being positive and movement of the heart towards the feet being negative left being negative. Lastly, the z-axis corresponds to accelerometer data 908 logging movement of the heart toward and away from the chest, with movement away from the chest being positive and back toward the chest being negative As shown therein, the basic ECG sinus rhythm, showing the characteristic QRS waveform, is shown at reference 902. From this, the heart rate may be monitored for the duration of the test. Below the ECG waveform 902, the x, y and z sensor data is shown, optionally color-coded for ease of reference although the waveforms appear in black and white in this document.

Significant to the operation of the SCG device 100 is the ability to detect, from the acquired x, y and z time-stamped accelerometer data, the opening and closing of the mitral and aortic valves. This data enables the calculation of the isovolumic contraction times and isovolumic relaxation times, which are key parameters in making an initial assessment of cardiac performance. The analysis of the acquired data may begin by identifying the isovolumic movement and then go forward and backward from that identified point to get the MVC and AVO parameters. As shown in FIG. 9, the isovolumic movement 910 is the largest negative-going waveform of z-axis trace 908. Looking at the other accelerometer data traces, trace 904 (x-axis, or side to side data) is moving toward the left arm but for identification, the accelerometer trace 908 is sufficient to identify the isovolumetric movement 910, whose amplitude is significant in detecting heart disease.

Figure 10:
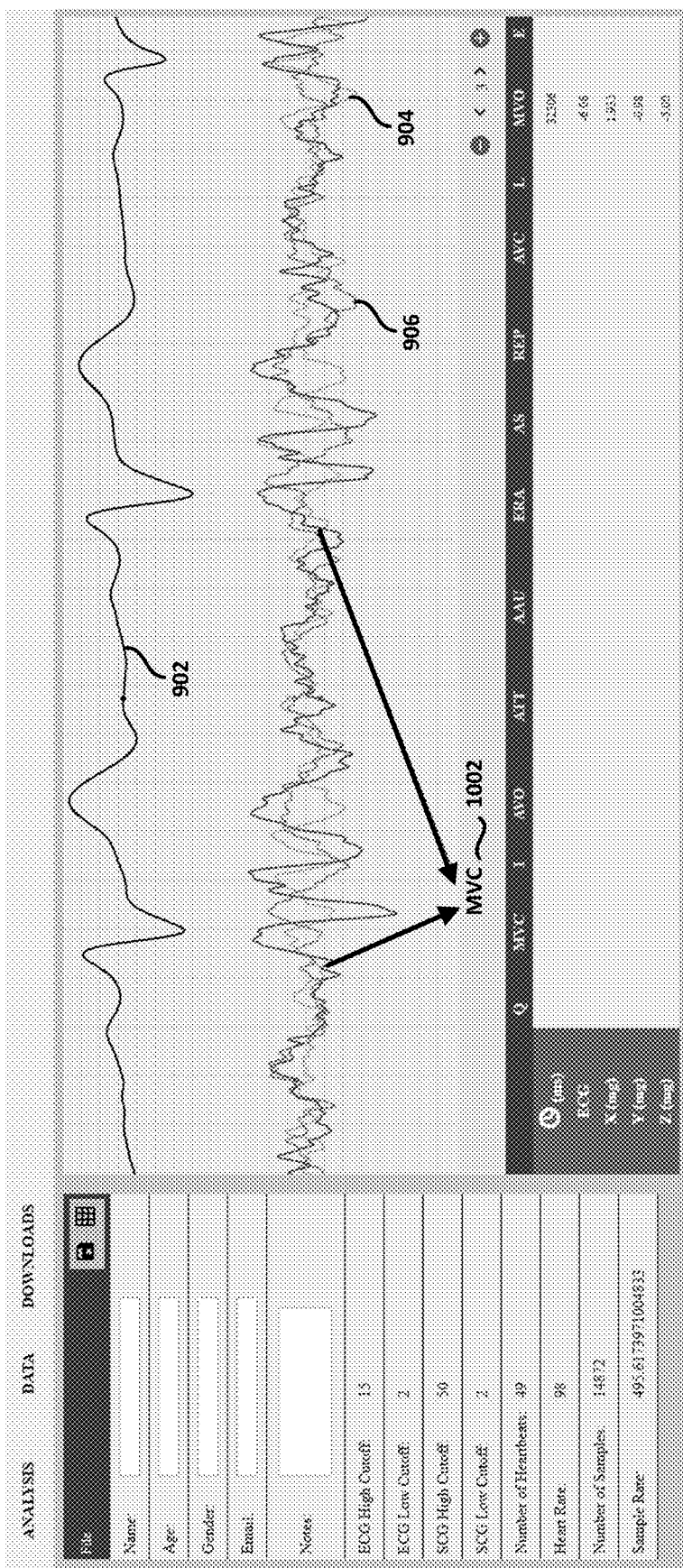
FIG. 10 shows a graph of the cardiac data acquired over time by an SCG device according to one embodiment, showing the identification of the closing of the mitral valve (MVC).

Shown in FIG. 10 is the waveform signature of the mitral valve close (MVC) event before the isovolumic movement, characterized by a rounded peak in advance of the isovolumetric movement 910. The onset of this peak is the MVC signal 1002.

Figure 11:
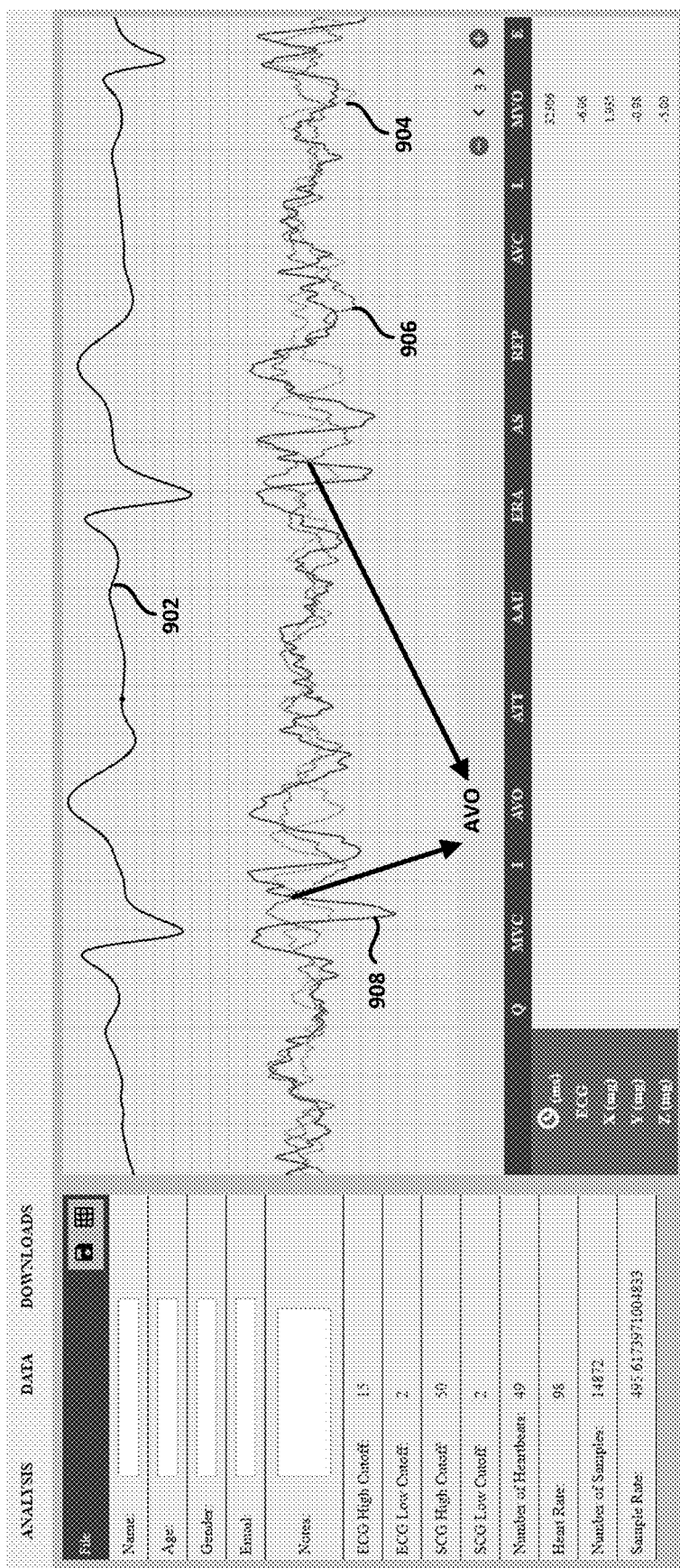
FIG. 11 shows a graph of the cardiac data acquired over time by an SCG device according to one embodiment, showing the identification of the aortic valve opening (AVO).

FIG. 11 shows the x, y and z accelerometer data acquired by the SCG device 100, showing identification of the aortic valve open or AVO. The isovolumic twist develops a force that is sufficient to open the AV valves. The valves opens but this does not create much of a seismic signal. As shown in FIG. 11, there is an upward direction change on the z-axis trace 908 and a direction change on both the x axis 904 and the y axis 906 accelerometer data. At the point where they cross with the positive going z-axis accelerometer data 908 is where the aortic valve opens; namely, the AVO point.

Figure 12:
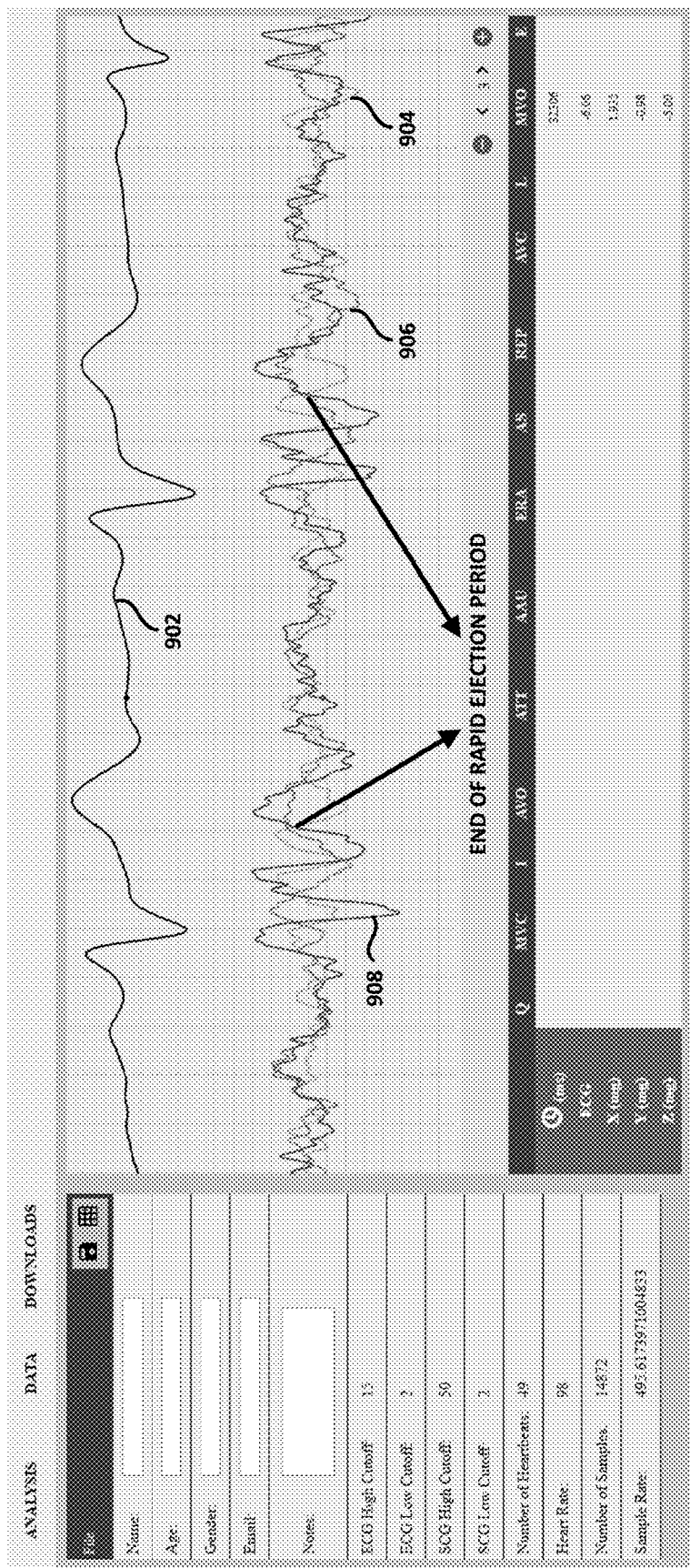
FIG. 12 shows a graph of the cardiac data acquired over time by an SCG device according to one embodiment, showing the identification of the end of the rapid ejection period.
Figure 13:
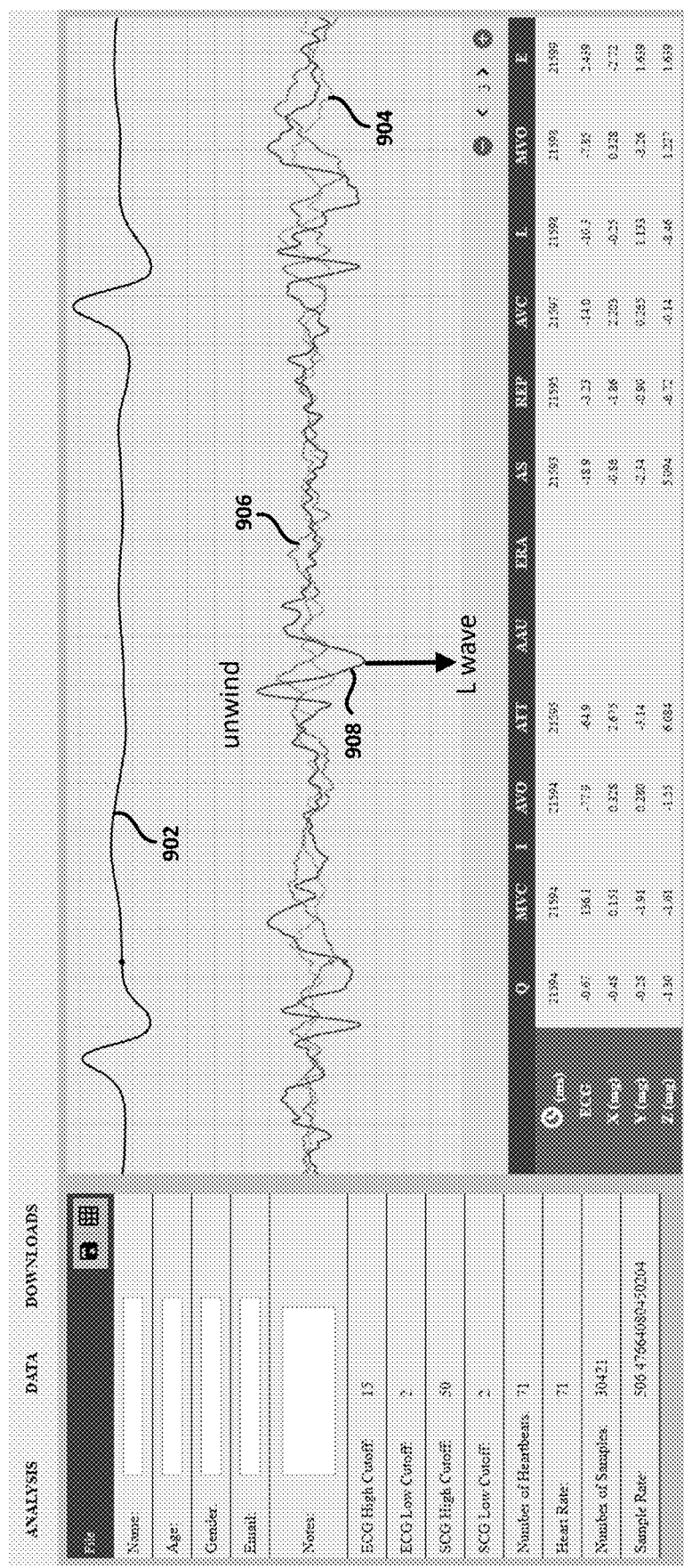
FIG. 13 shows a graph of the cardiac data acquired over time by an SCG device according to one embodiment, showing the identification of the L wave from three-axis SCG data.
Figure 14:
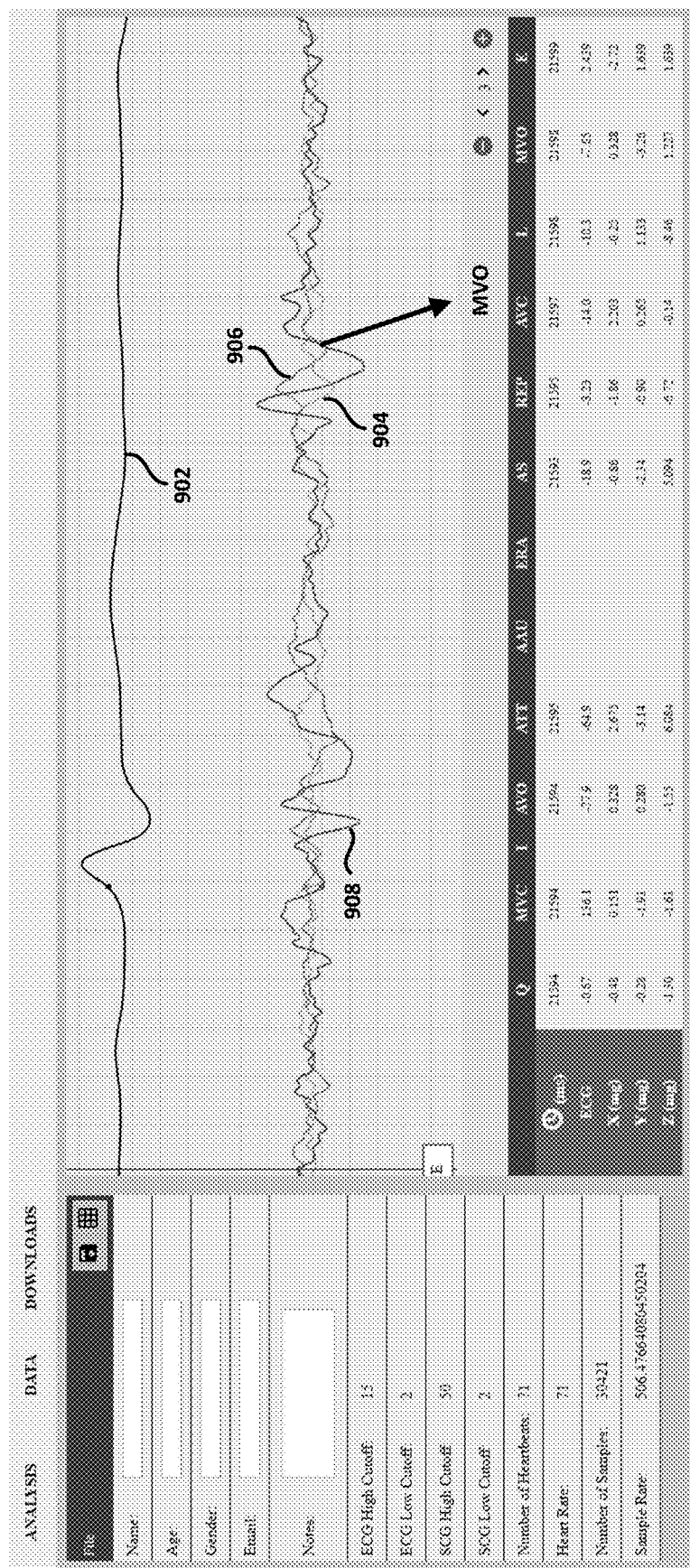
FIG. 14 shows a graph of the cardiac data acquired over time by an SCG device according to one embodiment, showing the identification of the opening of the mitral valve (MVO).
Figure 15:
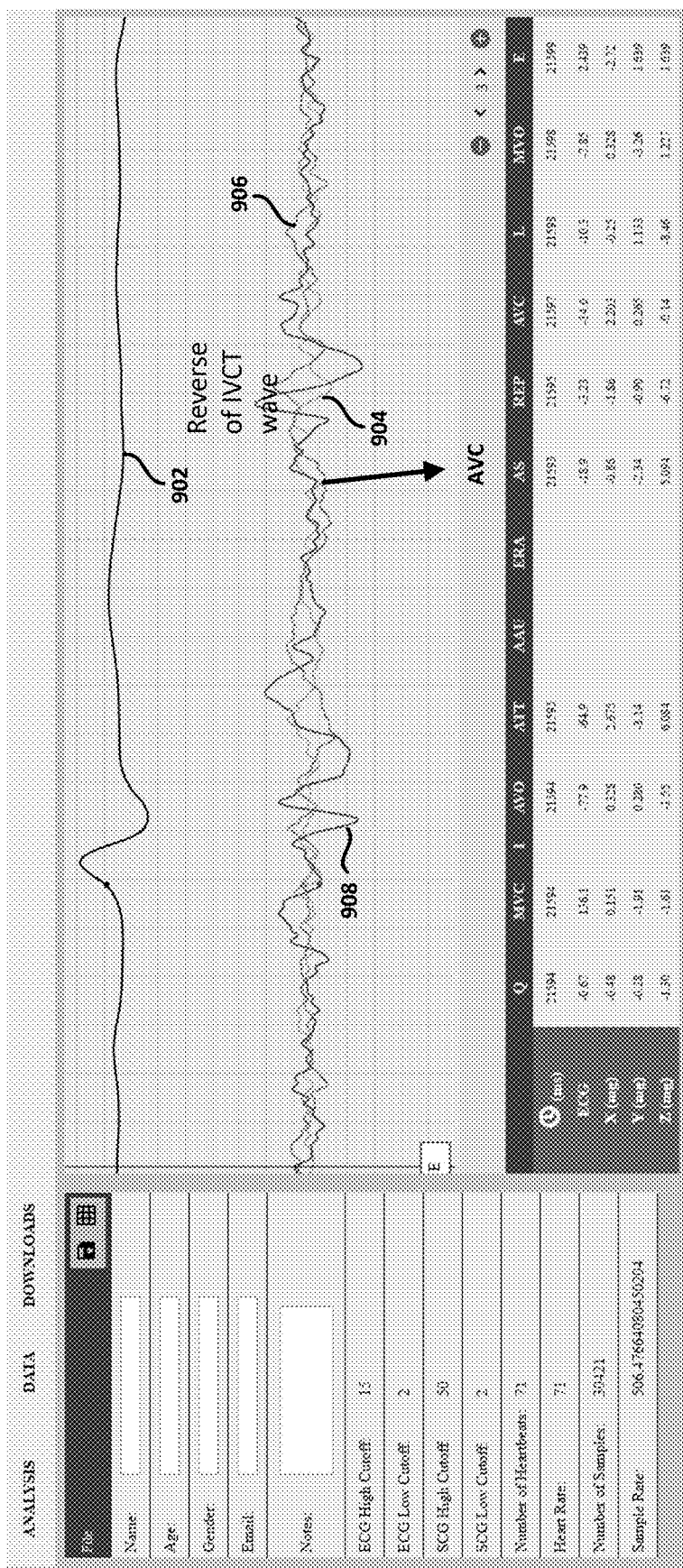
FIG. 15 shows a graph of the cardiac data acquired over time by an SCG device according to one embodiment, showing the closure of the aortic valve (AVC).

The next time the accelerometers cross is at the end of the rapid ejection period. The ventricle stops acceleration and resets to a relaxed position, as shown in FIG. 12. Thereafter, the diastolic signals are identified. The first signal of interest is the resetting of the ventricle after the aortic valve closes. FIG. 13 shows the portion of the accelerometer trace 908 identified as the L wave. Once the L wave is identified, the mitral valve open signal MVO may be identified as being located on the upslope of the ascending signal and is identified by the other accelerometers, as shown in FIG. 14. Lastly, as the aortic valve closes quietly, the only indication is a toward-the-back movement as the aorta recoils after closure. The detected AVC is shown in FIG. 15. Other ways of detecting the AVC are possible. Following the closure, the ventricle untwists with a reverse of the isovolumic contraction wave. The next event is the early diastolic filling, whereupon the cycle repeats. For at least some of these identified fiduciary markers, comparison with threshold values may help identify them as being normal or potentially abnormal. Moreover, comparing like measured or derived parameters over time may help in identifying beneficial or detrimental changes in the functioning of the heart muscle.

The SCG heart data (i.e., the acquired and time-stamped digitized movement vectors) may then be uploaded, while keeping the present SCG device turned on. The date and time of any recordings stored on the device will be displayed. Once the upload is complete, a heart health data report may then be generated and presented to the user, showing the user's heart rate in beats per minute (bpm), and an indication of the quality of the recording as "Good", "OK" or "Bad". The SCG data recording may also be carried out independently (i.e., without) involvement of the mobile device app. A "Bad" quality indication may result in the device prompting the user to repeat the test, taking care to snuggly position the SCG device on his or her chest to ensure reliable readings.

The data for each individual heart, therefore, has a number of so-called fiduciary points or markers. These may include the aforementioned atrial systole (AS), mitral valve closure (MVC), aortic valve opening (AVO), isovolumic contraction (IC) rapid ejection period (REP), aortic valve closure (AVC), mitral valve opening (MVO), early diastole (E wave or rapid filling) and the derived isovolumic contraction time (IVCT), and isovolumic relaxation time (IVRT). Surprisingly and unexpectedly, the combination of these fiduciary markers appear to be unique to each individual and may, therefore, be used to positively identify the person. The stored and/or contemporaneously-acquired heart data as described herein, therefore, may be used, alone or in combination with other biometric indicators, to identify people in high security situations, site access control and the like. The cardiac data so acquired is generally invariable over reasonable periods of time and does not change unless there is ischemia or damage from an infarct. Surprisingly, over several thousand testing sessions, it became clear that specific individual users, using the fiduciary markers, could be positively identified without any name after a just a few tests. One embodiment, therefore, of the present SCG device 100 may be used to positively identify the user, independent of any provided personal identifying information. Indeed, by comparing recently-acquired heart data of one person of a plurality of persons with previously-acquired heart data of the plurality of persons, a match (or a partial match that meets a predetermined similarity threshold) may be used to verify the identity of the person with a high degree of confidence, as the fiduciary markers, taken in the aggregate, may be seen to be the cardiac-analogue to fingerprints, unique to each individual.

An echocardiogram looks for heart abnormalities in the motion of the heart wall, which is how physicians identify ischemia and cardiac infarcts. The present SCG device acquires detailed and fine-grained measures of heart wall movement using three spatial vectors, which enables the generation of a profile of normal amplitudes and direction of change, using a single lead, a handheld device and a mobile device. For example, mitral or aortic insufficiency or stenosis is apparent in the data collected by the present SCG device as a noticeable extra signal representative of regurgitant flow or jetting across the aortic valve. This and similar telltale signals are easily spotted as sharp changes in direction during the aortic valve opening or closing timing, IVCT and IVRT.

Other applications include the force of ventricular contraction. This manifests itself as a twist force, which may be calculated from a combination of the time-dependent x, y and z-axis accelerometer data. The untwist mechanics of the heart may also reveal themselves as the magnitude of the L-wave as a percentage of I-wave (twist of the ventricle) and this ratio may be used to determine the level of fitness of the user. Also, changes in the MVO opening, as evidenced by successive SCG testing sessions over a period of time may correlated with changes in stress or fatigue. Many other physiological parameters, measurements and calculations may be made once a precise, time-stamped three-dimensional representation of the movement of the heart is acquired and stored. Machine learning techniques may be employed to good effect on anonymized 3-D cardiac data acquired by the present SCG devices to identify heart function disorders and degradations, and to identify clusters of users with particular ailments and generally to deduce heart-related information across users, in large populations. In turn, this may lead to pre-emptive heart health care initiatives and advance the state of the art in cardiac care and public health.

One embodiment, therefore, is a seismocardiography system comprising a wireless tri-axial seismocardiography (SCG) device. According to one embodiment, the SCG device may comprise a housing comprising a skin contact surface configured to contact skin of a user's chest wall and an outer surface disposed away from and facing away from the skin contact surface; and a printed circuit board (PCB) disposed in the housing. The PCB is configured to support and interconnect a processor; a three-axis accelerometer module comprising an Inertial Measurement Unit (IMU); a communication module configured to communicate with an app on a mobile device and with a remote server over a computer network; a power source; a time base; and memory. The processor may be configured to cause the IMU of the three-axis accelerometer module, when the device is positioned on the user's chest in a predetermined orientation during a test, to detect, sample and digitize movement vectors of the user's chest caused by the user's heart beats over a predetermined period of time in each of x, y and z directions, and to store the digitized movement vectors in the memory together with time-stamp information generated by the time base and to send the time-stamped digitized movement vectors to at least one of the app on the mobile device and the remote server using the communication module.

According to further embodiments, the system may comprise a chest strap configured to encircle the user's chest, or a single gel-electrode that can be secured to the chest sternum, to record the heart activity from the user's chest wall. In one embodiment, the remote server may be configured to recognize, from the time-stamped digitized movement vectors, a plurality of fiduciary markers in a cardiac cycle of the user. The remote server may be configured to generate, from the time-stamped digitized movement vectors, a heart performance index configured to provide an indication of health and fitness of the user's heart and to send the generated heart performance index to the mobile device for display to the user. The remote server may be further configured to recognize a plurality of fiduciary markers, from the time-stamped digitized movement vectors, the fiduciary markers including at least some of atrial systole (AS); mitral valve closure (MVC); aortic valve opening (AVO); isovolumic contraction (IC); rapid ejection period (REP); aortic valve closure (AVC); mitral valve opening (MVO), and early diastole (E wave or rapid filling). The remote server may be further configured to calculate, from at least some of the fiduciary markers, at last one of isovolumic contraction time (IVCT) isovolumic relaxation time (IVRT) systolic ejection period and diastolic period and to generate a Heart Performance Index therefrom, and to send the generated Heart Performance Index to the mobile device for display to the user by the app. The remote server may be further configured to detect, changes to at least some of IVCT, IVRT, systolic ejection period and diastolic period over consecutive tests and to provide therefrom indicators of changes over time in the efficiency of the user's heart.

According to one embodiment, the processor, the three-axis accelerometer module, and the time base may be configured to sample and digitize the movement vectors of the user's chest in each of x, y and z directions at least as often as every 2 ms within a range of at least +/−2 g at an acceleration resolution of 0.25 mg or smaller. Other specifications may be implemented. The time-stamped digitized movement vectors may be configured to enable at least the remote server to determine a rate and manner with which the user's heart twists and untwists across the x, y and z axes over time. The time-stamped digitized movement vectors may be configured to enable at least the remote server to identify mitral or aortic insufficiency or stenosis as sharp changes in direction during isovolumic contraction time (IVCT) and isovolumic relaxation time (IVRT).

Another embodiment is a computer-implemented method, comprising a wireless tri-axial seismocardiography (SCG) device configured to measure and time-stamp movements of a user's chest caused by the user's heart beats; positioning the SCG device on the user's chest in a predetermined orientation and initiating a test; using the positioned SCG device, detecting, sampling, digitizing and time-stamping movement vectors of the user's chest over a predetermined period of time in each of x, y and z directions; storing the time-stamped digitized movement vectors in a memory of the SCG device and sending the time-stamped digitized movement vectors to at least one of the app on the mobile device and the remote server over a computer network; receiving, by the app on the mobile device, a plurality of fiduciary markers from the remote server, the plurality of fiduciary markers being detected from or derived using the time-stamped digitized movement vectors in each of x, y and z directions; and generating a report on the mobile device using at least some of the plurality of fiduciary markers, the report including an indication of the health of the user's heart.

According to further embodiments, providing may be carried out with the SCG device comprising a housing comprising a skin contact surface configured to contact skin of the user's chest and an outer surface disposed away from and facing away from the skin contact surface, a printed circuit board (PCB) disposed in the housing and configured to support and interconnect a processor, a three-axis accelerometer module comprising an Inertial Measurement Unit (IMU), a communication module configured to communicate with the app on the mobile device and with the remote server over a computer network, a power source, a time base and the memory. The computer-implemented method may further comprise the remote server generating, from the sent time-stamped digitized movement vectors, a heart performance index configured to provide an indication of health and fitness of the user's heart and sending the generated heart performance index to the mobile device for display to the user. The method may further comprise the remote server analyzing the time-stamped digitized movement vectors and identifying a plurality of fiduciary markers therein, the fiduciary markers including at least some of atrial systole (AS); mitral valve closure (MVC); aortic valve opening (AVO); isovolumic contraction (IC); rapid ejection period (REP); aortic valve closure (AVC); mitral valve opening (MVO), and early diastole (E wave or rapid filling).

In one embodiment, the remote server may be configured to calculate, from the identified fiduciary markers, at last one of isovolumic contraction time (IVCT), isovolumic relaxation time (IVRT), systolic ejection period and diastolic period to enable a generation of a heart performance index therefrom and a display of the generated heart performance index on the app of the mobile device. The method may further comprise the remote server calculating changes to at least some of IVCT, IVRT, systolic ejection period, and diastolic period over consecutive tests and to providing therefrom indicators of changes in the efficiency of the user's heart for display on the app of the mobile device. The SCG device may be configured to sample and digitize the movement vectors of the user's chest in each of x, y and z directions, for example, at least as often as every 2 ms within a range of at least +/−2 g at an acceleration resolution of 0.25 mg or smaller. The computer-implemented method may further comprise the remote server determining, from the time-stamped digitized movement vectors, a rate and manner with which the user's heart twists and untwists across the x, y and z axes over time. The remote server may be configured to identify, from the time-stamped digitized movement vectors, sharp changes in direction during isovolumic contraction time (IVCT), and isovolumic relaxation time (IVRT) as indicators of mitral or aortic insufficiency or stenosis.

It is to be understood that the present computer-implemented method may be configured such that the SCG device carries out some or all of the calculations and computations disclosed above to be carried out by the remote server(s). Likewise, rather than the remote server(s) carrying out the above-disclosed calculations and computations, some or all may be carried out by the user's mobile device or in part by the present SCG device, in part by the user's mobile device (and, optionally in part by a remote server). Indeed, one embodiment has the SCG device and/or the user's mobile device carry out all of the above-detailed analyses and computations, thereby obviating the need to upload the encrypted digitized movement vectors to the remote server over the network, other than for disaster-proofing and long-term storage, for example.

Yet another embodiment is a computer-implemented method, comprising providing at least one wireless tri-axial seismocardiography (SCG) device configured to measure and time-stamp movements of a user's chest caused by the user's heart beats; using the provided at least one SCG device, carrying out at least one test for each of a plurality of users. Each test may comprise positioning the SCG device on the user's chest in a predetermined orientation; using the positioned SCG device, sampling, digitizing and time-stamping movement vectors of the user's chest over a predetermined period of time in each of x, y and z directions; sending the time-stamped digitized movement vectors to a remote server over a computer network; identifying and storing, by the remote server, a set of fiduciary markers in each test using the time-stamped digitized movement vectors in each of x, y and z directions and associating each the sets of fiduciary markers with a predetermined one of the plurality of users. Thereafter, the method may further comprise subsequently testing of one of the plurality of users and generating a corresponding time-stamped digitized movement vectors; generating a subsequent set of fiduciary markers using the corresponding time-stamped digitized movement vectors in each of x, y and z directions; comparing the corresponding fiduciary markers generated during the subsequent test with the stored sets of fiduciary markers to identify at least one matching set of stored fiduciary markers; and identifying which of the plurality of users was subsequently tested as the predetermined user whose associated set of stored fiduciary markers at least partially matches the corresponding fiduciary markers generated during the subsequent test.

Further, the SCG device, the user's mobile device and the remote server(s) are described as carrying specific roles, computations and calculations. However, any of these roles, computations and calculations may be carried out in whole or in part by the SCG device, the user's mobile device or the remote servers. Indeed, offloading heart health index, fiduciary marker computations to the remote server(s) and/or the user's mobile device is a design choice and may be guided by cost-effectiveness considerations, among others. These may also be carried out internally by the present SCG device, given sufficient computing power and memory resources. Therefore, embodiments are not to be limited by which of the SCG device, the user's mobile device and the remote server(s) carry out which computation and functions. These may be distributed at will, to best leverage the available computational resources in each of these devices.

Portions of the detailed description above describe processes and symbolic representations of operations by computing devices that may include computer components, including a local processing unit, memory storage devices for the local processing unit, display devices, and input devices. Furthermore, such processes and operations may utilize computer components in a heterogeneous distributed computing environment including, for example, remote file servers, computer servers, and memory storage devices. These distributed computing components may be accessible to the local processing unit by a communication network.

The processes and operations performed by the computer include the manipulation of data bits by a local processing unit and/or remote server and the maintenance of these bits within data structures resident in one or more of the local or remote memory storage devices. These data structures impose a physical organization upon the collection of data bits stored within a memory storage device and represent electromagnetic spectrum elements. Moreover, the computer-implemented methods disclosed herein improve the functioning of computers by a user to administer self-test and to obtain therefrom a detailed analysis of the health and efficiency of his or her heart, and to generate a detailed history of fiduciary markers that are useful in tracking the efficiency of the heart over time. Such computer-implemented methods are not capable of being effectively carried out by the mental processes of humans.

A process, such as the computer-implemented methods described and shown herein, may generally be defined as being a sequence of computer-executed steps leading to a desired result. These steps generally require physical manipulations of physical quantities. Usually, though not necessarily, these quantities may take the form of electrical, magnetic, or optical signals capable of being stored, transferred, combined, compared, or otherwise manipulated. It is conventional for those skilled in the art to refer to these signals as bits or bytes (when they have binary logic levels), pixel values, works, values, elements, symbols, characters, terms, numbers, points, records, objects, images, files, directories, subdirectories, or the like. It should be kept in mind, however, that these and similar terms should be associated with appropriate physical quantities for computer operations, and that these terms are merely conventional labels applied to physical quantities that exist within and during operation of the computer.

It should also be understood that manipulations within the computer are often referred to in terms such as adding, comparing, moving, positioning, placing, illuminating, removing, and altering and the like. The operations described herein are machine operations performed in conjunction with various input provided by a human or artificial intelligence agent operator or user that interacts with the computer. The machines used for performing the operations described herein include local or remote general-purpose digital computers or other similar computing devices.

In addition, it should be understood that the programs, processes, methods, etc. described herein are not related or limited to any particular computer or apparatus nor are they related or limited to any particular communication network architecture. Rather, various types of general-purpose hardware machines may be used with program modules constructed in accordance with the teachings described herein. Similarly, it may prove advantageous to construct a specialized apparatus to perform the method steps described herein by way of dedicated computer systems in a specific network architecture with hard-wired logic or programs stored in nonvolatile memory, such as read only memory.

While certain example embodiments have been described, these embodiments have been presented by way of example only, and are not intended to limit the scope of the embodiments disclosed herein. Thus, nothing in the foregoing description is intended to imply that any particular feature, characteristic, step, module, or block is necessary or indispensable. Indeed, the novel methods and systems described herein may be embodied in a variety of other forms; furthermore, various omissions, substitutions and changes in the form of the methods and systems described herein may be made without departing from the spirit of the embodiments disclosed herein.

While certain embodiments of the disclosure have been described, these embodiments have been presented by way of example only, and are not intended to limit the scope of the disclosure. Indeed, the novel methods, devices and systems described herein may be embodied in a variety of other forms. Furthermore, various omissions, substitutions and changes in the form of the methods and systems described herein may be made without departing from the spirit of the disclosure. The accompanying claims and their equivalents are intended to cover such forms or modifications as would fall within the scope and spirit of the disclosure. For example, those skilled in the art will appreciate that in various embodiments, the actual physical and logical structures may differ from those shown in the Figures. Depending on the embodiment, certain steps described in the example above may be removed, others may be added. Also, the features and attributes of the specific embodiments disclosed above may be combined in different ways to form additional embodiments, all of which fall within the scope of the present disclosure. Although the present disclosure provides certain preferred embodiments and applications, other embodiments that are apparent to those of ordinary skill in the art, including embodiments which do not provide all of the features and advantages set forth herein, are also within the scope of this disclosure. Accordingly, the scope of the present disclosure is intended to be defined only by reference to the appended claims.

The invention claimed is:

1. A system, comprising: a wireless tri-axial seismocardiography device, comprising: a housing comprising a skin contact surface configured to contact skin of a user's chest wall and an outer surface disposed away from and facing away from the skin contact surface; and a printed circuit board (PCB) disposed in the housing and configured to support and interconnect: a processor; a three-axis accelerometer module comprising an Inertial Measurement Unit (IMU); a communication module configured to communicate with an software application on a mobile device and with a remote server over a computer network; a power source; a time base; and memory; wherein, the processor is configured to cause the IMU of the three-axis accelerometer module, when the device is positioned on the user's chest in a predetermined orientation during a test, to detect, sample and digitize movement vectors of the user's chest caused by the user's heart beats over a predetermined period of time in each of x, y and z directions, and to store the digitized movement vectors in the memory together with time-stamp information generated by the time base and to send the time-stamped digitized movement vectors to at least one of the software application on the mobile device and the remote server using the communication module, the remote server being configured to determine, solely from the time-stamped digitized movement vectors, a unique plurality of fiduciary markers in at least one cardiac cycle of the user and, based on the unique plurality of fiduciary markers, positively determine an identity of the user from amongst a plurality of users by at least partially matching the determined unique plurality of fiduciary markers with previously-acquired cardiac data of the user, the remote server being configured to generate, from the time-stamped digitized movement vectors, a heart performance index configured to provide an indication of health and fitness of the identified user's heart and to send the generated heart performance index to the mobile device to be displayed to the identified user.

2. The system of claim 1, further comprising at least one of a chest strap configured to encircle the user's chest and to secure the device onto the user's chest wall and a single gel-electrode configured to attach to a lower part of the sternum.

3. The system of claim 1, wherein the fiduciary markers are determined along with a time and force measurement and include at least some of:
   atrial systole (AS);
   mitral valve closure (MVC);
   aortic valve opening (AVO);
   isovulumic contraction (IC);
   rapid ejection period (REP);
   aortic valve closure (AVC);
   mitral valve opening (MVO), and
   early diastole (E wave or rapid filling).

4. The system of claim 3, wherein the remote server is further configured to calculate, from at least some of the fiduciary markers, at least one of isovolumic contraction time (IVCT), isovolumic relaxation time (IVRT), systolic ejection period and diastolic period and to generate a heart performance index therefrom and to send the generated heart performance index to the mobile device to be displayed to the user by the software application.

5. The system of claim 4, wherein the remote server is further configured to detect, changes to at least some of IVCT, IVRT, systolic ejection period and diastolic period over consecutive tests and to provide therefrom indicators of changes over time in the efficiency of the user's heart and to determine systolic heart performance and diastolic heart performance.

6. The system of claim 1, wherein the processor, the three-axis accelerometer module, and the time base are collectively configured to sample and digitize the movement vectors of the user's chest in each of x, y and z directions at least as often as every 2 ms within a range of at least +/−2 g at an acceleration resolution of 0.25 mg or smaller.

7. The system of claim 1, wherein the time-stamped digitized movement vectors are configured to enable at least the remote server to determine a rate and manner with which the user's heart twists and untwists across the x, y and z axes over time.

8. The device of claim 1, wherein the time-stamped digitized movement vectors are configured to enable at least the remote server to identify mitral or aortic insufficiency or stenosis as sharp changes in direction during isovolumic contraction time (IVCT) and isovolumic relaxation time (IVRT).

9. A computer-implemented method, comprising: providing a wireless tri-axial seismocardiography (SCG) device configured to measure and time-stamp movements of a user's chest caused by the user's heart beats; positioning the SCG device on the user's chest in a predetermined orientation and initiating a test; using the positioned SCG device, detecting, sampling, digitizing and time-stamping movement vectors of the user's chest over a predetermined period of time in each of x, y and z directions; storing the time-stamped digitized movement vectors in a memory of the SCG device and sending the time-stamped digitized movement vectors to at least one of the software application on the mobile device and a remote server over a computer network; receiving, by the software application on the mobile device, a plurality of fiduciary markers from the remote server, the plurality of fiduciary markers being detected from or derived using the time-stamped digitized movement vectors in each of x, y and z directions, the remote server having determined an identity of the user by at least partially matching the plurality of fiduciary markers with previously-acquired cardiac data of the user; and generating a report on the mobile device using at least some of the plurality of fiduciary markers, the report including an indication of the health of the identified user's heart.

10. The computer-implemented method of claim 9, wherein providing is carried out with the SCG device comprising a housing comprising a skin contact surface configured to contact skin of the user's chest and an outer surface disposed away from and facing away from the skin contact surface, a printed circuit board (PCB) disposed in the housing and configured to support and interconnect a processor, a three-axis accelerometer module comprising an Inertial Measurement Unit (IMU), a communication module configured to communicate with the software application on the mobile device and with the remote server over a computer network, a power source, a time base and the memory.

11. The computer-implemented method of claim 9, further comprising the remote server generating, from the sent time-stamped digitized movement vectors, a heart performance index configured to provide an indication of health and fitness of the user's heart and sending the generated heart performance index to the mobile device for display to the user.

12. The computer-implemented method of claim 9, further comprising the remote server analyzing the time-stamped digitized movement vectors and identifying a plurality of fiduciary markers therein, the fiduciary markers including at least some of:
    atrial systole (AS);
    mitral valve closure (MVC);
    aortic valve opening (AVO);
    isovolumic contraction (IC);
    rapid ejection period (REP);
    aortic valve closure (AVC);
    mitral valve opening (MVO), and
    early diastole (E wave or rapid filling).

13. The computer-implemented method of claim 12, further comprising the remote server calculating, from the identified fiduciary markers, at last one of isovolumic contraction time (IVCT), isovolumic relaxation time (IVRT), systolic ejection period and diastolic period to enable a generation of a heart performance index therefrom and a display of the generated heart performance index on the software application of the mobile device.

14. The computer-implemented method of claim 13, further comprising the remote server calculating changes to at least some of IVCT, IVRT, systolic ejection period and diastolic period over consecutive tests and to providing therefrom indicators of changes in the efficiency of the user's heart for display on the software application of the mobile device.

15. The computer-implemented method of claim 9, further comprising configuring the SCG device to sample and digitize the movement vectors of the user's chest in each of x, y and z directions at least as often as every 2 ms within a range of at least +/−2 g at an acceleration resolution of 0.25 mg or smaller.

16. The computer-implemented method of claim 9, further comprising the remote server determining, from the time-stamped digitized movement vectors, a rate and manner with which the user's heart twists and untwists across the x, y and z axes over time.

17. The computer-implemented method of claim 9, further comprising the remote server to identifying, from the time-stamped digitized movement vectors, sharp changes in direction during isovolumic contraction time (IVCT) and isovolumic relaxation time (IVRT) as indicators of mitral or aortic insufficiency or stenosis.

18. A computer-implemented method, comprising:
    providing at least one wireless tri-axial seismocardiography (SCG) device configured to measure and time-stamp movements of a user's chest caused by the user's heart beats;
    using the provided at least one SCG device, carrying out at least one test for each of a plurality of users, each test comprising:
        positioning the SCG device on the user's chest in a predetermined orientation;
        using the positioned SCG device, detecting, sampling, digitizing and time-stamping movement vectors of the user's chest over a predetermined period of time in each of x, y and z directions;
        sending the time-stamped digitized movement vectors to a remote server over a computer network;
        identifying and storing, by the remote server, a set of fiduciary markers in each test using the time-stamped digitized movement vectors in each of x, y and z directions;
    associating each the sets of fiduciary markers with a predetermined one of the plurality of users,
    subsequently testing of one of the plurality of users and generating corresponding time-stamped digitized movement vectors;
    generating a subsequent set of fiduciary markers using the corresponding time-stamped digitized movement vectors in each of x, y and z directions;
    comparing the corresponding fiduciary markers generated during the subsequent test with the stored sets of fiduciary markers to identify at least one matching set of stored fiduciary markers;
    identifying which of the plurality of users was subsequently tested as the predetermined user whose associated set of stored fiduciary markers at least partially matches the corresponding fiduciary markers generated during the subsequent test, and
    causing a report to be displayed on a mobile device of the identified user using at least some of the corresponding fiduciary markers generated during the subsequent test, the report including an indication of the health of the identified user's heart.

\* \* \* \* \*